(12) United States Patent
DeBusk et al.

(10) Patent No.: US 9,922,304 B2
(45) Date of Patent: Mar. 20, 2018

(54) SYSTEM FOR SENSING AND RECORDING CONSUMPTION OF MEDICAL ITEMS DURING MEDICAL PROCEDURE

(71) Applicant: DeRoyal Industries, Inc., Powell, TN (US)

(72) Inventors: Brian C. DeBusk, Knoxville, TN (US); Mary E. Kaylor, Chattanooga, TN (US); Gerald T. Griffith, Knoxville, TN (US); Timothy J. Waggoner, Ringgold, GA (US); Jeffrey D. Griffith, Knoxville, TN (US); Angela M. Sewell, Knoxville, TN (US); John G. Jacobs, Knoxville, TN (US); Rex A. Hurd, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 759 days.

(21) Appl. No.: 14/504,859

(22) Filed: Oct. 2, 2014

(65) Prior Publication Data

US 2015/0127362 A1 May 7, 2015

Related U.S. Application Data

(60) Provisional application No. 61/900,064, filed on Nov. 5, 2013, provisional application No. 61/993,578, filed
(Continued)

(51) Int. Cl.
*G06Q 10/08* (2012.01)
*G06F 19/00* (2018.01)
(Continued)

(52) U.S. Cl.
CPC ......... *G06Q 10/087* (2013.01); *G06F 19/327* (2013.01); *G06F 19/328* (2013.01); *G06K 7/10316* (2013.01); *G06Q 50/22* (2013.01)

(58) Field of Classification Search
CPC .... G06Q 10/087; G06Q 50/22; G06F 19/327; G06F 19/328; G06K 7/10316
See application file for complete search history.

(56) References Cited

U.S. PATENT DOCUMENTS

| 5,779,053 A | 7/1998 | Partika et al. |
| 5,991,728 A | 11/1999 | DeBusk et al. |

(Continued)

FOREIGN PATENT DOCUMENTS

WO 2006026365 A2 3/2006

OTHER PUBLICATIONS

WaveMark brochure, WaveMark CIMS™ Clinical Inventory Management Solution, WaveMark, Inc., Sep. 20, 2010.
(Continued)

*Primary Examiner* — Linh Giang Le
(74) *Attorney, Agent, or Firm* — Luedeka Neely Group PC

(57) ABSTRACT

An apparatus senses and records consumption of medical items during performance of a medical procedure. The medical items are enclosed in wrappers having RFID tags in which medical item information is encoded. The apparatus includes a shielded enclosure that attenuates radio frequency signals emanated from RFID tags disposed outside the shielded enclosure to levels that are substantially undetectable within the internal space. RFID antennas inside the shielded enclosure receive radio frequency signals emanated from RFID tags on wrappers that are removed from used items and placed inside the enclosure. An RFID reader decodes the medical item information encoded in the RFID tags. A computer processor executes a medical item inventory module including instructions for generating a post-op list of medical items consumed during the medical procedure. Item billing information and usage trend information
(Continued)

may be derived from the post-op list. Also, Latex alerts and item expiration alerts may be generated based on information encoded in the RFID tags.

28 Claims, 20 Drawing Sheets

Related U.S. Application Data on May 15, 2014, provisional application No. 62/048,921, filed on Sep. 11, 2014.

(51) Int. Cl.
*G06Q 50/22* (2018.01)
*G06K 7/10* (2006.01)

(56) References Cited

U.S. PATENT DOCUMENTS

| | | | |
|---|---|---|---|
| 5,995,937 A | 11/1999 | DeBusk et al. | |
| 6,014,633 A | 1/2000 | DeBusk et al. | |
| 6,812,838 B1 | 11/2004 | Maloney | |
| 7,639,136 B1 | 12/2009 | Wass et al. | |
| 7,689,316 B1 | 3/2010 | Frederick et al. | |
| 7,938,326 B2 | 5/2011 | Dearing et al. | |
| 7,942,321 B2 | 5/2011 | Linton et al. | |
| 7,990,272 B2 | 8/2011 | Wass et al. | |
| 8,174,392 B1 | 5/2012 | Saghbini et al. | |
| 8,281,994 B1 | 10/2012 | Wass et al. | |
| 8,346,632 B2 | 1/2013 | Saghbini | |
| 8,461,962 B2 | 6/2013 | Philippe | |
| 2003/0009354 A1 | 1/2003 | Arbogast et al. | |
| 2003/0046111 A1 | 3/2003 | Snitkin | |
| 2004/0046020 A1 | 3/2004 | Andreasson et al. | |
| 2006/0259377 A1 | 11/2006 | Fedor et al. | |
| 2007/0222599 A1* | 9/2007 | Coveley | A61B 5/1113 340/572.4 |
| 2008/0030345 A1 | 2/2008 | Austin et al. | |
| 2008/0077433 A1 | 3/2008 | Kasprisin et al. | |
| 2008/0202357 A1* | 8/2008 | Flood | B30B 9/3007 100/35 |
| 2008/0215363 A1 | 9/2008 | Kasprisin et al. | |
| 2009/0027164 A1 | 1/2009 | Hara | |
| 2010/0079240 A1 | 4/2010 | Higham | |
| 2010/0094649 A1 | 4/2010 | White | |
| 2010/0106515 A1 | 4/2010 | McCoy | |
| 2010/0138238 A1 | 6/2010 | Sable | |
| 2010/0141457 A1* | 6/2010 | Wass | G06Q 10/08 340/572.8 |
| 2010/0161345 A1 | 6/2010 | Cain et al. | |
| 2010/0198611 A1 | 8/2010 | Ruoff et al. | |
| 2010/0262432 A1 | 10/2010 | Benja-Athon | |
| 2010/0274585 A1 | 10/2010 | Philippe | |
| 2011/0010275 A1 | 1/2011 | Hull | |
| 2011/0077969 A1 | 3/2011 | Zhu et al. | |
| 2011/0173028 A1 | 7/2011 | Bond | |
| 2013/0060577 A1 | 3/2013 | DeBusk et al. | |
| 2013/0088354 A1* | 4/2013 | Thomas | A61B 90/96 340/572.1 |
| 2013/0124227 A1* | 5/2013 | Ellis | G06Q 10/06 705/3 |
| 2013/0191149 A1* | 7/2013 | Kolberg | G06F 19/3456 705/3 |
| 2013/0278067 A1* | 10/2013 | Poss | B65F 1/0033 307/62 |
| 2014/0163726 A1 | 6/2014 | Shoenfeld et al. | |

OTHER PUBLICATIONS

Specification Sheet for WaveMark CIMS™ Intelligent Storage Units and Usage Tracking, WaveMark, Inc., Feb. 11, 2010.

DOC 2.0 User Manual; DeRoyal Order Connection User Documentation (49 pages); May 2009; DeRoyal Industries, Inc.; United States.

DOC Trauma User Manual; DeRoyal Trauma User Documentation (57 pages); DeRoyal Industries, Inc.; United States.

\* cited by examiner

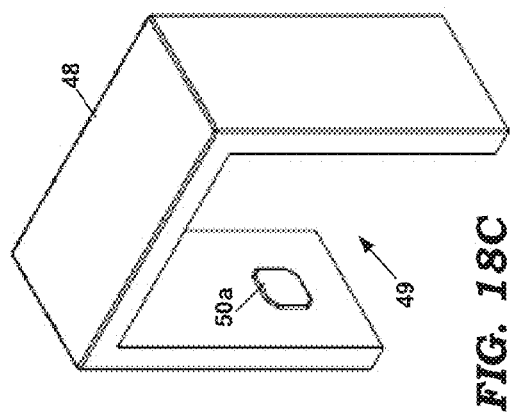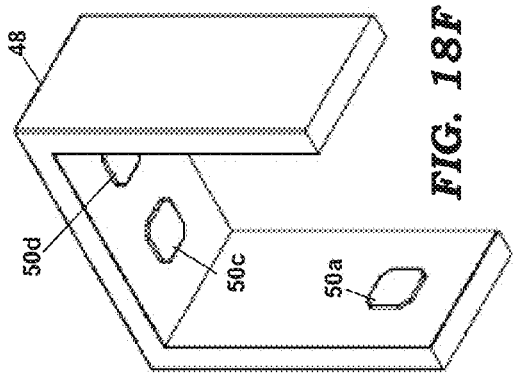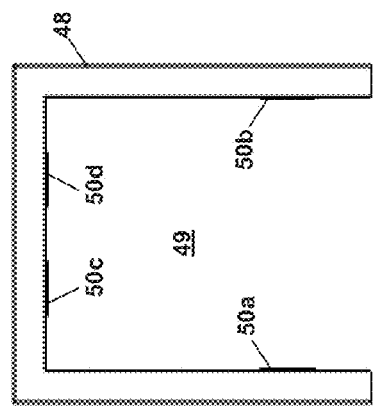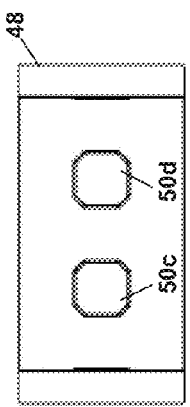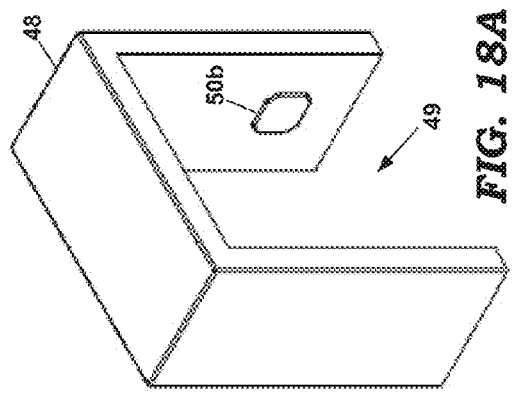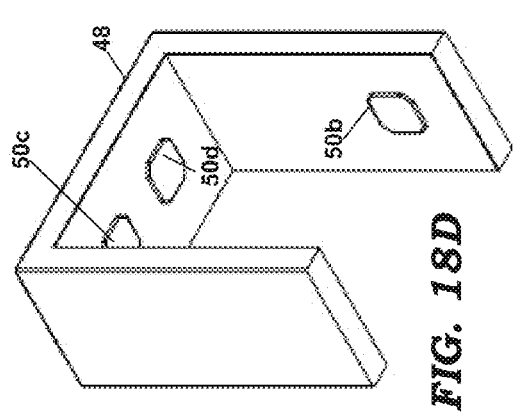

SYSTEM FOR SENSING AND RECORDING CONSUMPTION OF MEDICAL ITEMS DURING MEDICAL PROCEDURE

RELATED APPLICATIONS

This application claims priority to U.S. provisional patent application Ser. Nos. 61/900,064, filed Nov. 5, 2013, titled "System for Sensing and Recording Consumption of Medical Items During Surgical Procedure," 61/993,578, filed May 15, 2014, titled "System for Sensing and Recording Consumption of Medical Items During Medical Procedure," and 62/007,601, filed Jun. 4, 2014, titled "Customer Management of Custom Medical Procedural Trays With E-Commerce Interface," the entire contents of which are incorporated herein by reference.

FIELD

This invention relates to the field of medical item inventory management. More particularly, this invention relates to a system for sensing and recording items that have been consumed during a medical procedure.

BACKGROUND

The use of medical supplies and sterile medical devices in the provision of health care services is one of the most significant expenses incurred by most health care facilities. Depending upon the nature and complexity of the medical procedure being performed, a large number of supply items may be used during a medical procedure and, given the priorities of medical personnel involved in the procedure, the ability to track the supplies, gather data about supply utilization and consumption, and record that data in a useable format can be especially difficult. While hospitals and other health care facilities may have sophisticated information systems related to supply inventory management and procedure-based supply requirements, such systems are not able to provide consistent data analysis of supply utilization and optimization if the usage data is not recorded diligently.

In a typical hospital, there are multiple different information systems that are utilized for managing supply inventory and for insuring that the proper supplies are provided for each medical procedure, such as a particular surgery. In the first instance, the hospital supply department will typically have an inventory management system that tracks medical supply inventory, identifies the location of that inventory and records inventory levels as supplies are withdrawn for usage or replaced with new shipments of supplies or re-stocks from previously withdrawn but unused supplies. This inventory management system typically tracks the location of supplies in multiple locations throughout the hospital. In some hospitals, this inventory process is still a manual process.

Another common type of information system in a typical hospital that interfaces with the inventory management system is the Operating Room Information System (ORIS). The typical ORIS will provide functionality such as scheduling the operating rooms for procedures, identifying the type of procedure to be performed, identifying the doctor performing the procedure, identifying the assisting nurse(s), and maintaining lists of supplies, devices and instruments (Bills of Materials, or BOM's) that should be provided for each procedure. Typically, these BOM's are specific to (1) the type of procedure being performed and (2) the physician performing the procedure. These BOM's are often maintained in a form known as Doctor Preference Cards.

It is common for the hospital inventory management system to interface with the ORIS in order to insure that the right supplies, devices and instruments are in stock and available for the upcoming scheduled medical procedures. Prior to each case, the BOM for a given procedure and physician is used to pull the appropriate supplies, devices and instruments for that case.

During the case, supply, device and instrument utilization for the procedure should be logged and unused items returned to inventory. When properly logged, useful data about supply utilization is captured and communicated to both the ORIS system and the inventory management system. That data can subsequently be used to capture cost information for the procedure, update the inventory system, prompt necessary re-orders and, as the data for multiple procedures and physicians is accumulated, to analyze supply cost and utilization information for optimization of BOM's to reduce supply waste and identify supply cost savings opportunities.

If accurate information about the consumption of supplies, devices and instruments is not captured, then the ability to identify savings opportunities or to accurately bill for all consumed supply items is lost. It is difficult to insure that this logging step is performed accurately and consistently, since the medical personnel are primarily concerned with insuring the success of the medical procedure. Often, the medical personnel do not have time during the procedure to manually log information into a computer for used items that do not include barcodes, or to scan the barcodes of used items that have barcodes. As a result, much of the information winds up being lost during the turnover of the medical procedure room from one case to another. Another problem with inaccurately recording usage information is the possibility of erroneously charging for items that were not used, which can raise regulatory issues.

The use of RFID tags as part of the inventory control system has potential to facilitate the logging of the supply consumption more accurately and efficiently.

SUMMARY

In one aspect, embodiments of the invention use Radio Frequency Identification (RFID) tags to provide the following general functions: (1) identifying medical items or other resources that enter a room or other space in a medical facility; (2) determining where those medical items or other resources came from; and (3) determining whether those medical items or other resources were consumed during a medical procedure performed in the room or space.

In preferred embodiments of the present invention, each item pulled for use during a particular medical procedure in accordance with the Bill of Materials (BOM) for the procedure and the physician includes an RFID tag affixed to the item's outer packaging. These RFID tags contain appropriate inventory information regarding each item as maintained in the inventory control system and the Operating Room Information System (ORIS). Each individual item that might be used can be tracked through use of the RFID tags and appropriate RFID reader technology.

In preferred embodiments, each Operating Room (OR) or other procedure room has a shielded enclosure with multiple RFID antennas disposed inside. Preferably, a waste bin or receptacle is disposed in the shielded enclosure. This shielded enclosure and an RFID reader connected to the antennas may be conveniently located near the location where the sterile medical supplies are typically opened by the circulating nurse or other OR personnel responsible for setting up the OR for each procedure, such as near the OR back table. The RFID reader is preferably configured so as to only sense RFID tags that are inside the enclosure and not to sense RFID tags outside the enclosure.

Some preferred embodiments include a portal containing multiple RFID antennas connected to an RFID reader for reading RFID tags on medial items that are passed through the portal. The RFID reader connected to the portal antennas is preferably configured so as to only sense RFID tags that are inside the portal and not to sense RFID tags outside the portal. Preferably, the portal is also conveniently located near the location where the sterile medical supplies are typically opened by the circulating nurse or other personnel responsible for setting up the room for each procedure. The portal may also be located in areas where supplies are stored outside the procedure room and at other transition locations in the medical facility.

Once the packaging of a medical supply is opened, that item is considered "consumed" because the packaging has been compromised and it cannot be re-stocked. In preferred embodiments, as the packaging of medical supply items having RFID tags are opened, the packaging is dropped into the waste bin inside the shielded enclosure and the reader reads the RFID tags on that packaging. The RFID reader is connected to a data collection interface, such as an ORIS computer terminal, a tablet computer or smart phone, and the consumption information for each item is logged.

This system provides an accurate way to track supply utilization that does not require additional data input steps from the OR personnel. Simply throwing the discarded packaging into a waste bin, which is normal procedure, allows for the RFID tagged supplies to be registered as consumed.

In a further preferred embodiment, a stock bin is provided. Prior to performance of a medical procedure, all RFID-tagged medical supply items that were pulled from the supply room or supply cabinet are placed in the stock bin, the stock bin is moved through the portal or is placed inside the shielded enclosure, and the RFID reader reads the data from the RFID tags on the packaging. In this manner, pre-op data regarding items pulled for use according to a particular BOM can be captured for a given case.

Following the conclusion of the procedure, all RFID-tagged medical supply items that have not been opened, which are thus eligible for re-stocking, are placed into the stock bin, the stock bin is moved through the portal or is placed inside the shielded enclosure, and the RFID reader reads the data from the RFID tags on the packaging. In this manner, post-op data regarding both consumption and non-consumption relative to a given BOM can be captured for a given case. In some embodiments, the RFID reader is connected through a data interface into the ORIS system or the inventory management system and the data regarding the non-consumed items are captured. The process preferably associates medical items (and/or their manufacturer's lot number) and instrument trays to specific patients in the event of a recall or negative occurrence that is determined post-case.

Once the pre-op data and post-op data are accurately collected, the data can be very useful in myriad ways. Since consumption data is accurately determined through the sensing of packaging in the waste bin, billing for medical items consumed in the case can be more accurately reflected on the patient's bill, allowing the hospital to more accurately charge for the procedure. If the stock bin option is included, this ensures that items pulled for the procedure that were detected in the pre-op scan, but were not consumed during the procedure are properly returned to inventory. This process also digitally tracks the movement of each item through various transition locations in the medical facility. This makes it possible to identify excessive handling of items and potential exposures to infectious patients.

More sophisticated data analysis can lead to significant cost improvements, such as by trending consumption and non-consumption for multiple procedures and doctors.

Some preferred embodiments provide an apparatus for sensing and recording consumption of medical items during performance of a medical procedure. The medical items are at least initially enclosed in wrappers having RFID tags disposed in or on the wrappers. Medical item information regarding the medical items is encoded in the RFID tags.

The apparatus includes a shielded enclosure having an internal space for receiving the wrappers of the medical items. The shielded enclosure is configured to attenuate radio frequency signals emanated from RFID tags disposed outside the shielded enclosure to levels that are substantially undetectable within the internal space.

The apparatus includes one or more RFID antennas disposed within the internal space of the shielded enclosure. The RFID antennas receive radio frequency signals emanated from RFID tags attached to the wrappers disposed within the internal space. The radio frequency signals contain the medical item information encoded in the RFID tags.

The apparatus also includes at least one RFID reader that is electrically connected to the RFID antennas. The RFID reader decodes the medical item information contained in the radio frequency signals emanated from the RFID tags.

The apparatus further includes a computer that is in electrical communication with the RFID reader. The computer has a processor for executing a medical item inventory module comprising instructions for receiving the medical item information decoded by the RFID reader and generating a post-op used-item list of medical items consumed during the medical procedure based on the medical item information encoded in the RFID tags attached to a used set of wrappers disposed in the internal space of the shielded enclosure.

In one preferred embodiment, the apparatus includes a portal having a portal opening and multiple RFID antennas having fields of view directed into the portal opening. The multiple RFID antennas receive radio frequency signals emanated from RFID tags attached to wrappers that are passed through the portal. In this embodiment, the apparatus also includes an RFID reader that is electrically connected to the plurality of RFID antennas of the portal. The RFID reader decodes the medical item information contained in the radio frequency signals emanated from the RFID tags.

The wrappers may comprise a pre-op set of wrappers that are passed through the portal opening prior to beginning the medical procedure. This pre-op set of wrappers enclose medical items that were picked from inventory to be consumed during the medical procedure. In a preferred embodiment, the medical item inventory module includes instructions for generating a pre-op list of medical items that were picked from inventory to be consumed during the medical procedure. The instructions generate the pre-op list based on medical item information encoded in RFID tags attached to the pre-op set of wrappers.

The wrappers may comprise an unused set of wrappers that are passed through the portal opening after completion of the medical procedure. This unused set of wrappers enclose medical items that were not consumed during the medical procedure. In a preferred embodiment, the medical item inventory module includes instructions for generating a post-op unused-item list of medical items that were not consumed during the medical procedure based on medical item information encoded in RFID tags attached to the unused set of wrappers.

In some embodiments, the medical item inventory module includes instructions for comparing the first and post-op unused-item lists to the pre-op list. A first alert message is generated if any item in the pre-op list does not appear in at least one of the post-op lists. A second alert message is generated if any item in the first or post-op unused-item list does not appear in the pre-op list.

In another aspect, the invention provides a method for sensing and recording consumption of medical items during performance of a medical procedure. In a preferred embodiment, the method includes the following steps:

(a) picking medical items from inventory that are enclosed in wrappers including RFID tags, wherein medical item information regarding the medical items is encoded in the RFID tags;

(b) during performance of the medical procedure, consuming at least some of the medical items picked in step (a);

(c) placing the wrappers of the medical items consumed during performance of the medical procedure into a shielded enclosure;

(d) using one or more RFID antennas disposed inside the shielded enclosure, receiving radio frequency signals emanated from RFID tags attached to the wrappers disposed in the shielded enclosure, where the radio frequency signals contain the medical item information encoded in the RFID tags;

(e) using an RFID reader electrically connected to the one or more RFID antennas, decoding the medical item information contained in the radio frequency signals emanated from the RFID tags;

(f) using a computer processor, generating a post-op used-item list of medical items consumed during the medical procedure based on the medical item information encoded in the RFID tags attached to the wrappers disposed in the shielded enclosure; and (g) using a computer processor, generating billing information based on the post-op used-item list of medical items consumed during the medical procedure.

Some preferred embodiments of the method also include:

(h) prior to step (b), passing the medical items picked in step (a) through an opening in a portal;

(i) using RFID antennas disposed in the opening of the portal, receiving radio frequency signals emanated from RFID tags attached to the wrappers of the medical items passed through the opening of the portal;

(j) using an RFID reader electrically connected to the RFID antennas disposed in the opening of the portal, decoding the medical item information contained in the radio frequency signals emanated from the RFID tags; and (k) using a computer processor, generating a pre-op list of medical items picked from inventory to be used during the medical procedure, the pre-op list generated based on the medical item information encoded in the RFID tags attached to the wrappers of the medical items passed through the opening of the portal in step (h).

In some embodiments, the pre-op list is compared to an item pick list for the scheduled procedure to ensure accuracy of the items picked.

Some preferred embodiments also include:

(l) after step (b), passing medical items picked in step (a) that were not consumed during performance of the medical procedure through the opening of the portal;

(m) using the RFID antennas disposed in the opening of the portal, receiving radio frequency signals emanated from RFID tags attached to the wrappers of the medical items passed through the opening of the portal;

(n) using the RFID reader electrically connected to the RFID antennas disposed in the opening of the portal, decoding the medical item information contained in the radio frequency signals emanated from the RFID tags; and (o) using a computer processor, generating a post-op unused-item list of medical items picked from inventory but not used during the medical procedure, the post-op unused-item list generated based on the medical item information encoded in the RFID tags attached to the wrappers of the medical items passed through the opening of the portal in step (l).

Some preferred embodiments also include:

(p) comparing the first and post-op unused-item lists to the pre-op list of medical items that were picked from inventory to be consumed during the medical procedure;

(q) generating a first alert message if any item in the pre-op list does not appear in at least one of the first and post-op unused-item lists; and (r) generating a second alert message if any item in the first or post-op unused-item list does not appear in the pre-op list.

In another aspect, the invention provides a method for sensing and recording consumption of medical items during performance of a medical procedure. A preferred embodiment of the method includes the following steps:

(a) sensing that a medical item having an RFID tag has entered a medical procedure room using an RFID sensor attached to a portal associated with the room; and (b) sensing that the medical item having the RFID tag has been consumed during the medical procedure using an RFID sensor associated with a waste container located in the room.

Some preferred embodiments also include:

(c) storing in a database a lot identification number associated with the medical item having the RFID tag, wherein the lot identification number identifies a manufacturer's lot number for the medical item;

(d) storing in the database a patient identification number associated with the patient on which the medical procedure was performed during which the medical item was consumed; and (e) associating in the database the lot identification number and the patient identification number based upon sensing that the medical item was consumed during performance of the medical procedure on the patient.

In another aspect, the invention provides a method for sensing and recording utilization of medical resources in performance of a medical procedure in a medical facility. A preferred embodiment of the method includes the following steps:

(a) attaching an RFID tag to each of a plurality of medical resources, the RFID tag containing medical resource information that uniquely identifies the medical resource on which the RFID tag is attached, the plurality of medical resources including a first medical resource;

(b) disposing a first portal at a first transition location within the medical facility, the first portal comprising a first portal opening and one or more first RFID antennas having fields of view directed to the first portal opening;

(c) disposing a second portal at a second transition location within the medical facility, the second portal comprising a second portal opening and one or more second RFID antennas having fields of view directed to the second portal opening;

(d) the one or more first RFID antennas receiving radio frequency signals emanated from an RFID tag attached to the first medical resource as the first medical resource passes through the first portal;

(e) the one or more second RFID antennas receiving radio frequency signals emanated from the RFID tag attached to the first medical resource as the first medical resource passes through the second portal;

(f) decoding the medical resource information contained in the radio frequency signals emanated from the RFID tag attached to the first medical resource;

(g) detecting the presence of the first medical resource at the first transition location, the detecting based on the medical resource information decoded from the radio frequency signals emanated from the RFID tag attached to the first medical resource passing through the first portal at the first transition location;

(h) detecting the presence of the first medical resource at the second transition location, the detecting based on the medical resource information decoded from the radio frequency signals emanated from the RFID tag attached to the first medical resource passing through the second portal at the second transition location;

(i) determining a travel route of the first medical resource based at least in part on a time of detection of the first medical resource at the first transition location relative to a time of detection of the first medical resource at the second transition location; and (j) creating a utilization profile for the first medical resource based on the travel route.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein:

FIG. 15 depicts a display screen displayed to a user of the system while performing the method depicted in FIG. 12 according to an embodiment of the invention;

FIG. 16 depicts a display screen displayed to a user of the system while performing the method depicted in FIG. 13 according to an embodiment of the invention;

FIG. 17 depicts a display screen displayed to a user of the system while performing the method depicted in FIG. 14 according to an embodiment of the invention;

FIGS. 18A-18F depict a portal according to an embodiment of the invention;

DETAILED DESCRIPTION

As the term is used herein, a "medical item" is an item, material or substance that is used or consumed during the performance of a medical procedure. For example, sponges, gloves and drapes are medical items. A surgical implant is another example of a medical item. Medical items comprise a subset of "medical resources." As the term is used herein, a "medical resource" is any item, person, piece of equipment, or space involved in providing medical services for a patient. For example, a gurney on which a patient lies during a surgical procedure is a medical resource. The doctor performing the procedure, the attending nurses, and the patient are also medical resources. An operating room is a medical resource.

Figure 1:
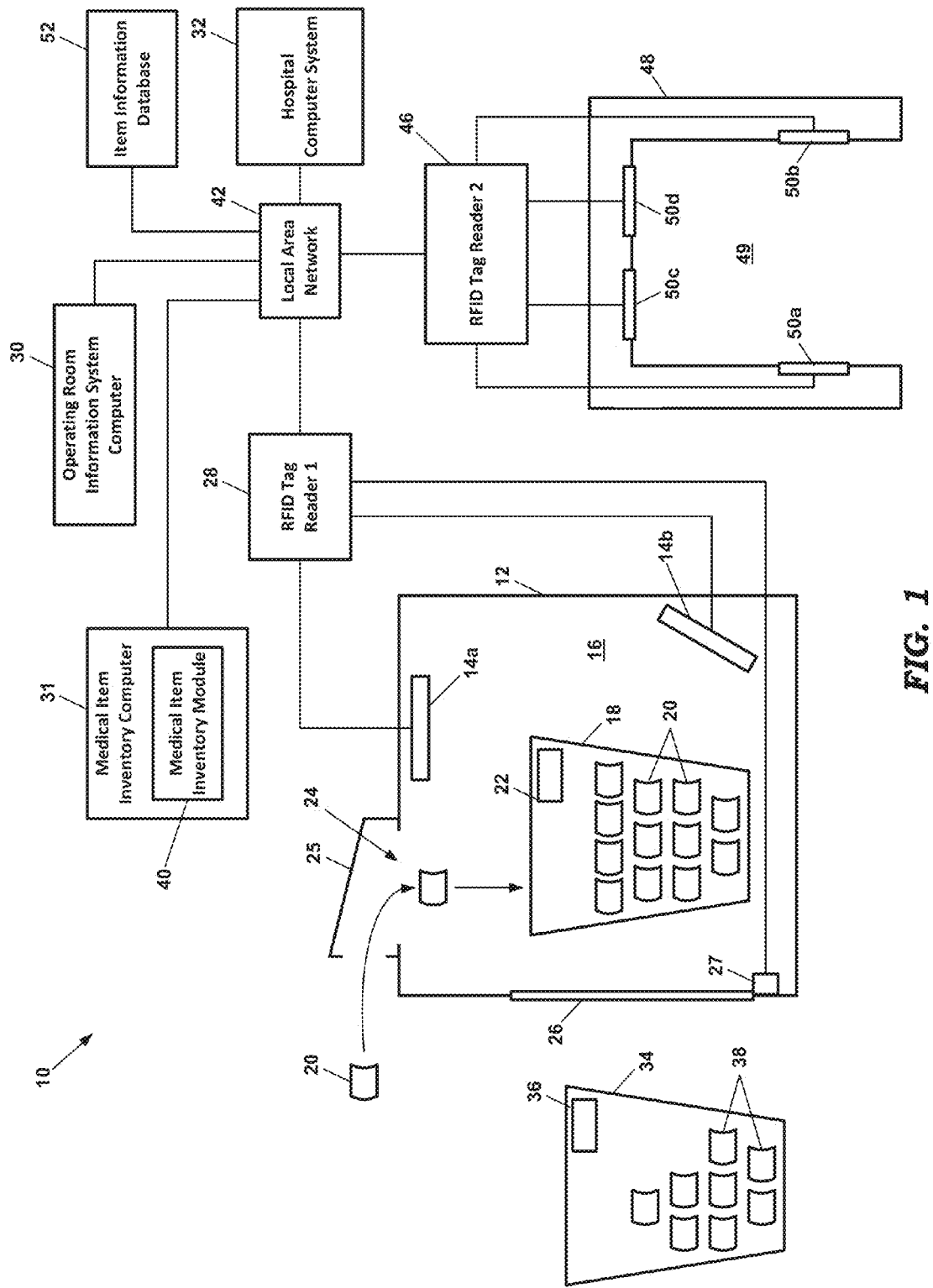
FIG. 1 depicts a system for sensing and recording consumption of medical items during a medical procedure according to an embodiment of the invention.

As shown in FIG. 1, a system 10 for sensing and logging consumption of medical items during a medical procedure includes a shielded enclosure 12 having a space 16 that is large enough to receive a waste bin 18. Disposed within the enclosure 12 are two RFID antennas 14a and 14b, such as Laird 5×5 inch Mini Far Field antennas (model number S9025PLNF) having left-hand circular polarization and operating in the 902-928 MHz frequency range. One of the antennas 14a is preferably disposed at the top of the enclosure 12, with its field of view looking downward into the space 16. The other RFID antenna 14b is preferably disposed at the bottom of the enclosure 12, with its field of view looking upward into the space 16. The RFID antennas 14a-14b are electrically connected, such as via a coaxial cable, to a UHF RFID tag reader 28. In a preferred embodiment, the RFID tag reader 28 is an Impinj® Speedway® model R420.

Figure 2B:
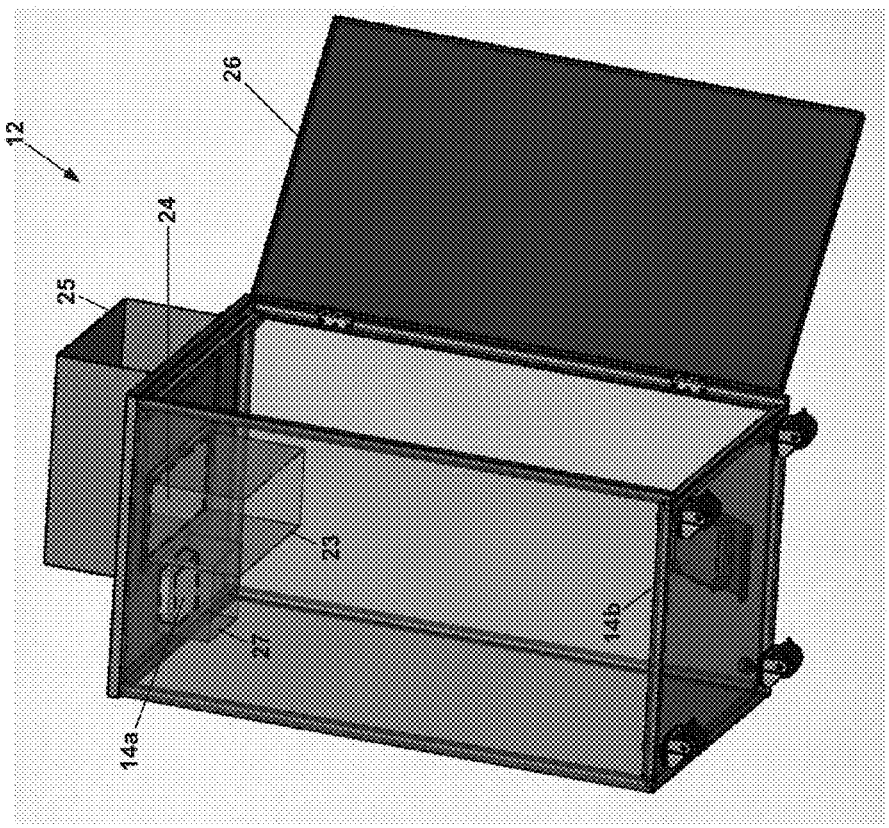
FIGS. 2A and 2B depict shielded enclosures according to embodiments of the invention.
Figure 2A:
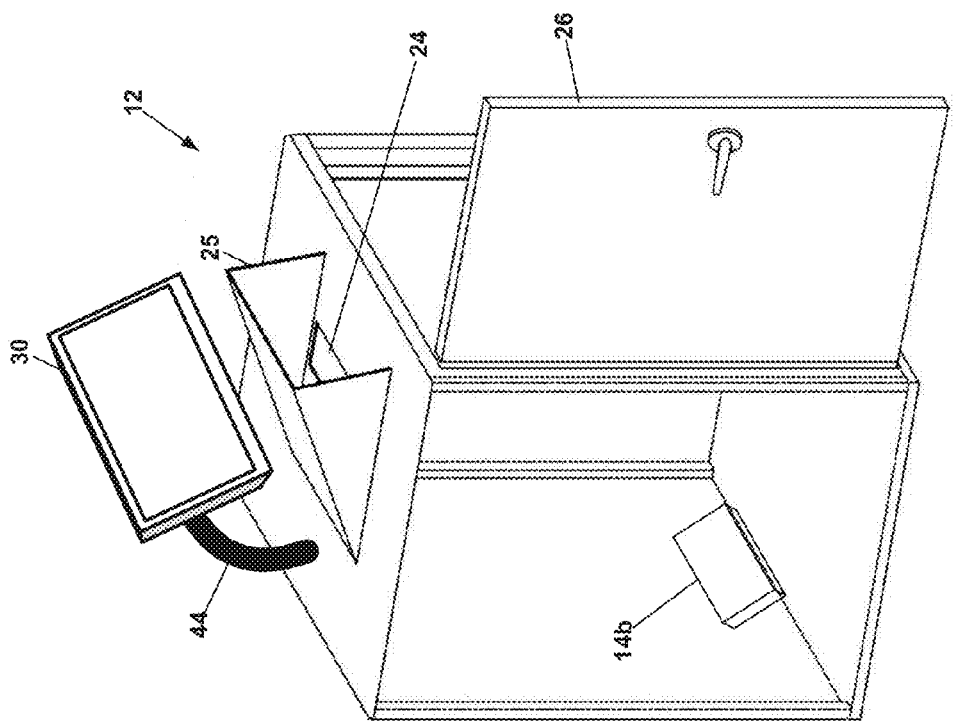

Preferred embodiments of the shielded enclosure 12 are shown in FIGS. 2A and 2B, wherein the sidewalls are depicted as transparent. The enclosure 12 is preferably made from 0.080 inch thick sheet aluminum supported by 0.75× 0.75 inch square aluminum tubing (0.125 thick). The outside dimensions of the preferred embodiment are 23.5×22.0× 40.75 inches.

As the term is used herein, "shielded" means that the enclosure 12 is designed to prevent the antennas 14a-14b from receiving RFID signals from RFID tags located outside the enclosure 12 at a signal-to-noise ratio high enough to trigger detection of those outside RFID tags. For purposes of this disclosure, "shielded" does not mean that absolutely all RF energy is blocked from entering the enclosure, as this would require unnecessary levels of shielding.

In some embodiments, an opening 24 is provided in the top of the enclosure that is large enough to receive wrappers or containers 20 from which medical items have been removed. The opening 24 is preferably a 6.75×13.75 inch rectangle. An aluminum cover 25 is provided over the opening 24. The cover may be slanted as shown in FIG. 2A or more box-like as shown in FIG. 2B to prevent signals from escaping the enclosure 12. As shown in FIG. 2B, the enclosure preferably includes an aluminum chute 23 around the opening 24, and an aluminum shield 27 around the antenna 14a. These structures provide further attenuation of RFID signals originating outside the enclosure 12 to prevent those signals from being detected by the antennas 14a-14b. The waste bin 18 is positioned below the opening 24 so that wrappers 20 deposited in the opening 24 fall into the bin 18. In a preferred embodiment, a hinged door 26 large enough to receive the waste bin 18 is provided in a sidewall of the enclosure 12. The door 26 is preferably 29.5×39.25 inch, and includes a handle/latch for securing the door in a closed position. The enclosure 12 is considered to be shielded when the door 26 is closed.

In a preferred embodiment, the system 10 includes a portal 48 having an opening 49 at least large enough to receive the waste bin 18. The portal 48 is preferably equipped with four RFID antennas 50a-50d having fields of view looking inward into the portal opening 49. The RFID antennas 50a-50d are electrically connected, such as via coaxial cables, to a UHF RFID tag reader 46. In a preferred embodiment, the RFID tag reader 46 is an Impinj® Speedway® model R220. In some embodiments, the tag reader 46 and the tag reader 28 comprise a single tag reader.

As the term is used herein, a "portal" is any passageway, opening, aperture, window, doorway, hallway, pathway, or aisle in or near which one or more RFID antennas are mounted for sensing RFID tags that pass through the portal. A portal may also be a handheld scanning device for reading RFID tags. Several portals may be used to track the routes of travel and locations of medical resources throughout a medical facility.

In preferred embodiments, portals are placed at "transition locations" within a medical facility. Examples of transition locations include supply rooms, supply cabinets, procedure rooms, waste containers, personnel break rooms, hallways, and points of entry into and exit from the medical facility.

As the term is used herein, a "wrapper" encompasses all manner of containers and packaging, sterile or non-sterile, in which a medical item is or has been enclosed. The term "wrapper" also includes a label, hang tag, or other such device that may be attached to a medical item without completely enclosing the item. The term "wrapper" further includes packaging for a sterile-wrapped kit of medical items, such as a tray of implants and supplies for use in a surgical procedure, wherein an RFID tag is attached to the tray. Generally, anything that may function to associate an RFID tag with a medical item is encompassed by the term "wrapper."

Each wrapper 20 includes an RFID tag attached thereto or embedded therein. Ultra High Frequency (UHF) passive RFID tags are preferred for this application, as they may be interrogated from up to about 30 centimeters away. In preferred embodiments, each RFID tag is encoded with a unique item identification number for the particular medical item associated with the wrapper. An item information database 52 associates each item identification number with item-specific information, such as the manufacturer part number, item description, vendor, cost, Latex content, expiration date, and inventory location. Additionally or alternatively, the RFID tag may be encoded with item-specific information as set forth in Unique Device Identification (UDI) standards set by the U.S. Food and Drug Administration (FDA).

In some embodiments, item-specific information encoded in RFID tags on medical items may be used to generate alerts for medical personnel. For example, an alert may be generated if information encoded in an RFID tag indicates the presence of Latex in an item, and the patient is allergic to Latex. Also, an alert may be generated if information encoded in an RFID tag indicates that an item's useful lifetime has expired or if the item is from a lot that has been recalled by the manufacturer.

The waste bin 18, also referred to herein as a waste tote, is preferably a plastic container having an open top for receiving wrappers 20. In some embodiments, an RFID tag 22 encoded with a unique bin identification number is attached to the waste bin 18. The database 52 associates the bin identification number with a particular procedure room to which the waste bin 18 is assigned. Alternatively, the RFID tag 22 may be encoded with information indicating the procedure room to which the bin 18 is assigned.

The RFID tag readers 28 and 46 are electrically connected via a local area network (LAN) 42 to a medical item inventory computer 31, which may be a server computer, desktop computer, laptop computer, tablet computer or other mobile computing device. Alternatively, the electrical connection between the RFID tag readers 28 and 46 and the computer 31 is via a Universal Serial Bus (USB) interface. The computer 31 includes memory for storing and a processor for executing instructions of a medical item inventory module 40. In preferred embodiments, the medical item inventory module 40 compiles pre-op and post-op lists of items, compares the lists to detect discrepancies, generates alert messages upon detection of discrepancies, and updates inventory records based on actual item usage.

In a preferred embodiment, an Operating Room Information System (ORIS) computer 30 is in communication with the medical item inventory computer 31 via a communication network, such as the LAN 42. The ORIS computer 30 is also in communication with a hospital computer system 32 via a communication network, such as the LAN 42. In preferred embodiments, the hospital computer system 32 manages medical item inventories, operating room scheduling, patient records, insurance reimbursement/payment functions, and admission/discharge/transfer (ADT) records. The hospital computer system 32 may also include or be connected to an electronic data interchange server, such as a J.D. Edwards/Oracle server, that implements electronic commerce transactions between the hospital and medical item suppliers.

In some embodiments, the medical item inventory module 40 is a software application running on the computer 31. In alternative embodiments, the medical item inventory module 40 is executed by a remote computer (outside the OR). For example, the medical item inventory module 40 may be implemented as "software-as-a-service" provided via the Internet by a medical item inventory service provider.

With continued reference to FIG. 1, a preferred embodiment of the system 10 includes a stock bin 34, which may also be referred to herein as a stock tote. As described in more detail below, the stock bin 34 is used to transfer medical items 38 to be used during a medical procedure from a stock room to the procedure room, and to transfer unused medical items 38 from the procedure room back to the stock room. In some embodiments, an RFID tag 36 is attached to the stock bin 34 that is encoded with a unique bin identification number. The database 52 associates the bin identification number with a particular procedure room or stock room to which the stock bin 34 is assigned. Alternatively, the RFID tag 36 may be encoded with information indicating the procedure room or stock room to which the stock bin 34 is assigned.

Figure 3:
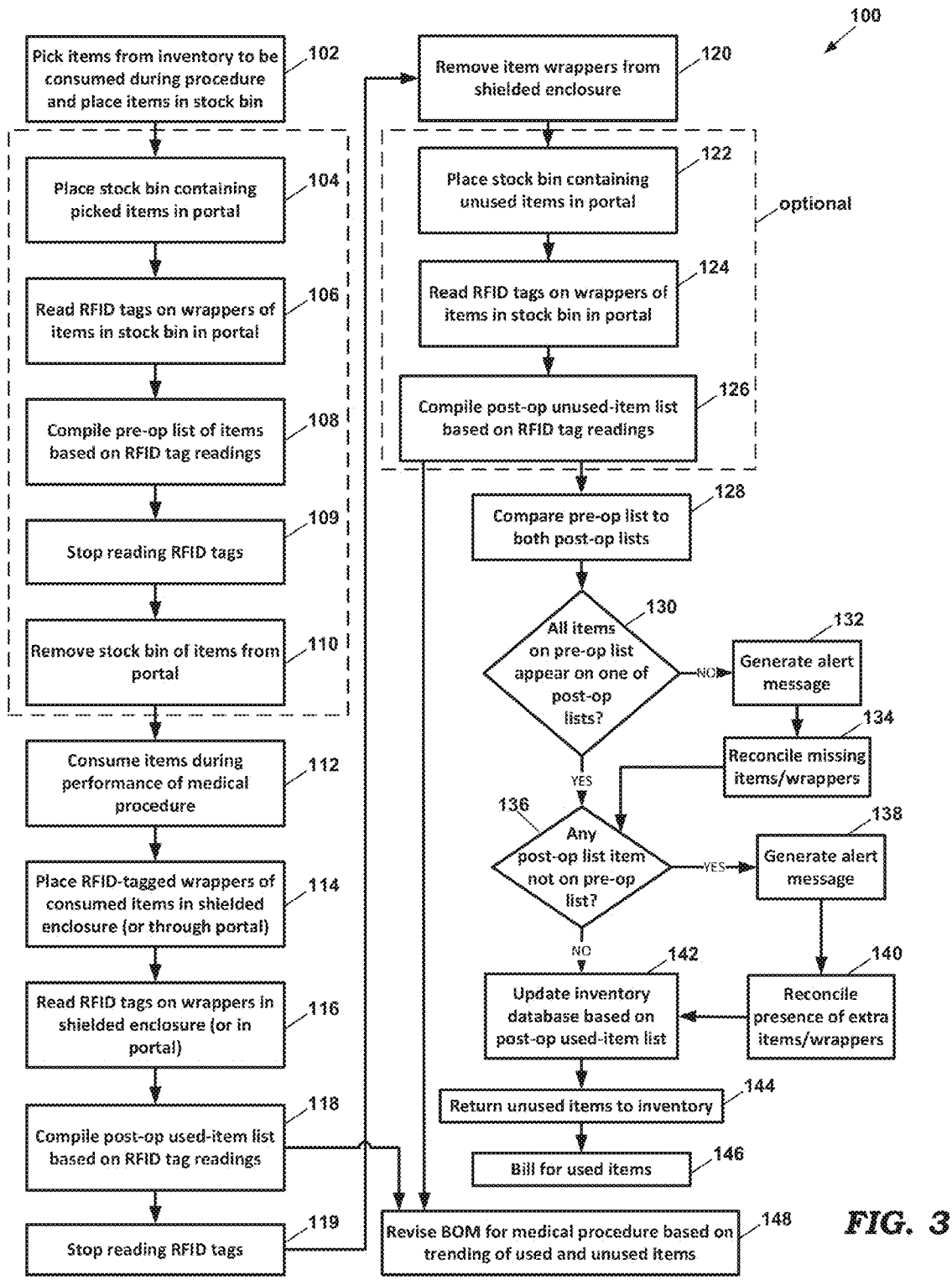
FIG. 3 depicts a method for sensing and recording consumption of medical items during a medical procedure according to an embodiment of the invention.

FIG. 3 depicts a preferred embodiment of a process 100 for sensing and recording consumption of medical items during a medical procedure using the system depicted in FIG. 1. To begin the process, hospital personnel pick medical items from inventory stock to be used during the medical procedure (step 102 in FIG. 3). For example, the needed items may be listed on a Bill of Materials (BOM) for the particular type of procedure to be performed. In some cases, the BOM also reflects the individual preferences of particular doctors. These types of BOM's may also be referred to as Doctor Preference Cards. The picked items are placed in the stock bin 34 to be transferred to the OR.

In one embodiment, the stock bin 34 containing the picked items 38 is placed in or passed through the portal 48 outside the procedure room (step 104) and the RFID reader 46 reads the RFID tags on the wrappers of the items 38 in the stock bin 34 (step 106). In some embodiments, activation of the reader 28 is triggered manually by a person in the procedure room using an interface device (mouse, touchpad or keyboard) of the computer 31.

The item identification numbers read from the RFID tags in the portal 48 are transferred to the medical item inventory computer 31 where the medical item inventory module 40 compiles a pre-op list of the items 38 in the stock bin 34 (step 108). In a preferred embodiment, the date/time of the compilation of the list is recorded in the medical item inventory computer 31, along with the identification number of the stock bin 34. Other information may be associated with the pre-op list, such as procedure room number, doctor name, patient name, patient age, patient weight, patient allergies, type of medical procedure, and case number. Once the pre-op list is compiled, the RFID reader 28 may be deactivated (step 109) and the stock bin 34 removed from the portal 48 (step 110).

Steps 104-110 of FIG. 3 are optional and are not implemented in all embodiments of process 100. If these steps are not performed, the BOM for the medical procedure may serve the purpose of the pre-op item list.

The items 38 are preferably removed from the bin 34 and arranged on a table in the procedure room according to the doctor's or attending nurse's preference. As the items 38 are used/consumed during the procedure (step 112), wrappers 20 removed from the items 38 are dropped through the opening 24 in the enclosure 12 where they are received into the waste bin 18 (step 114). When the wrappers 20 enter the enclosure 12, the RFID tags on the wrappers 20 are detected and read by the reader 28 (step 116). It will be appreciated that a waste bin 18 is not absolutely necessary for this process. However, the use of a waste bin 18 makes collection and removal of the wrappers 20 easier.

The item identification numbers read from the RFID tags in the enclosure 12 are transferred to the medical item inventory computer 31 where the medical item inventory module 40 compiles a post-op used-item list of the wrappers 20 (step 118). In a preferred embodiment, the date/time that each wrapper 20 was first detected is recorded in the list. Also, the identification number of the waste bin 18 (if any) and other information may be associated with the post-op used-item list, such as procedure room number, doctor name, patient name, type of medical procedure, and case number. Once the post-op used-item list is compiled, the RFID reader 28 is deactivated (step 119) so that it will not read any other tags when the door 26 is opened to remove the wrappers 20 (step 120). Deactivation of the reader 28 may be triggered by opening the door 26 of the enclosure 12.

In an alternative embodiment, the waste bin 18 remains outside the shielded enclosure 12 during the procedure. As the items 38 are used/consumed during the procedure (step 112), wrappers 20 removed from the items 38 are deposited in the waste bin 18. After completion of the procedure, the waste bin 18 containing the wrappers 20 is placed through the portal 48 (step 114), and the reader 28 reads the RFID tags of the wrappers 20 (step 116). The post-op used-item list is compiled as described in the previous embodiment (step 118).

In some embodiments, after completion of the medical procedure, all unused items 38 are placed back into the stock bin 34, and the stock bin 34 is passed through the portal 48 (step 122). The reader 28 reads the RFID tags of the unused items 38 (step 124), and a post-op unused-item list is compiled (step 126). The identification number of the stock bin 34 and other information may be associated with the post-op unused-item list, such as procedure room number, doctor name, patient name, type of medical procedure, and case number.

Steps 122-126 of FIG. 3 are optional and are not implemented in all embodiments of process 100. If these steps are not performed, the post-op unused-item list may be generated by comparing the BOM to the post-op used item list.

Various embodiments of the invention use the pre-op and post-op item lists to implement various advantageous inventory and billing functions. For example, the medical item inventory module 40 may compare the items listed in the pre-op list to the items listed in the post-op used-item list and the post-op unused-item list (step 128). If an item in the pre-op list does not appear on either of the post-op lists (step 130), this means the item was brought into the procedure room but neither the item nor its wrapper ended up in the stock bin or the waste bin after the procedure. In this case, an alert is generated that causes a message to appear on a display screen of the ORIS computer 30 or the medical item inventory computer 31 (step 132). The alert should prompt the procedure room personnel to investigate three possibilities that may have caused the discrepancy: (1) the item is unused and still in the procedure room but was inadvertently not placed back into the stock bin before the post-op unused-item list was compiled, (2) the item was used and its wrapper is still in the procedure room but the wrapper was inadvertently not placed in the waste bin before the post-op used-item list was compiled, or (3) the item and/or its empty wrapper was removed from the procedure room prior to compilation of either of the post-op lists. In any event, the missing item(s) or wrapper(s) should be located and the pre-op and post-op lists reconciled (step 134).

If the comparison of the pre-op and post-op item lists indicates that an item that appears on either of the post-op lists is not on the pre-op list (step 136), this means that the item or its wrapper was present in the procedure room when the post-op lists were compiled, but it was (1) not brought into the procedure room in the stock bin with the other items, or (2) brought into the procedure room in the stock bin but was removed from the stock bin prior to compilation of the pre-op list. In this case, an alert is generated which causes a message to appear on a display screen of the computer 31 (step 138). The alert should prompt the procedure room personnel to investigate what may have caused the discrepancy and reconcile the pre-op and post-op lists (step 140).

In a preferred embodiment, once the post-op lists are complete and reconciled, the computer 31, the ORIS computer 30, or the hospital computer system 32 uses the lists to update the database 52 based on actual item usage (step 142). The hospital computer system 32 or the ORIS computer 30 also may use the post-op used-item list to accurately bill the patient (or insurance company) for the items used during the procedure (step 146). The stock bin 34 may be returned to the appropriate inventory stock room where the unused items 38 may be returned to inventory (step 144).

In preferred embodiments, the hospital computer system 32 or the Medical Item Inventory Application 40 analyzes the post-op unused-item lists generated during multiple procedures of the same type and for the same doctor to determine trends in the lack of usage of certain medical items that are listed on BOM's (step 146). This trend data may be used to revise the BOM's for certain procedures/ doctors. For example, if the trend data indicates that in 90% of hip replacement surgeries performed by Dr. Jones only three sponges of a particular type are used out of the five called for on the BOM, the BOM may be revised to call for only three sponges. Revisions of this sort would reduce the effort/cost associated with returning unused items to the stock room, and would decrease traffic in and out of the procedure room during a procedure which would decrease the chances of a site infection. Trend data may also be used to determine the optimal locations to store medical supplies and the optimal quantities to store.

Figure 4:
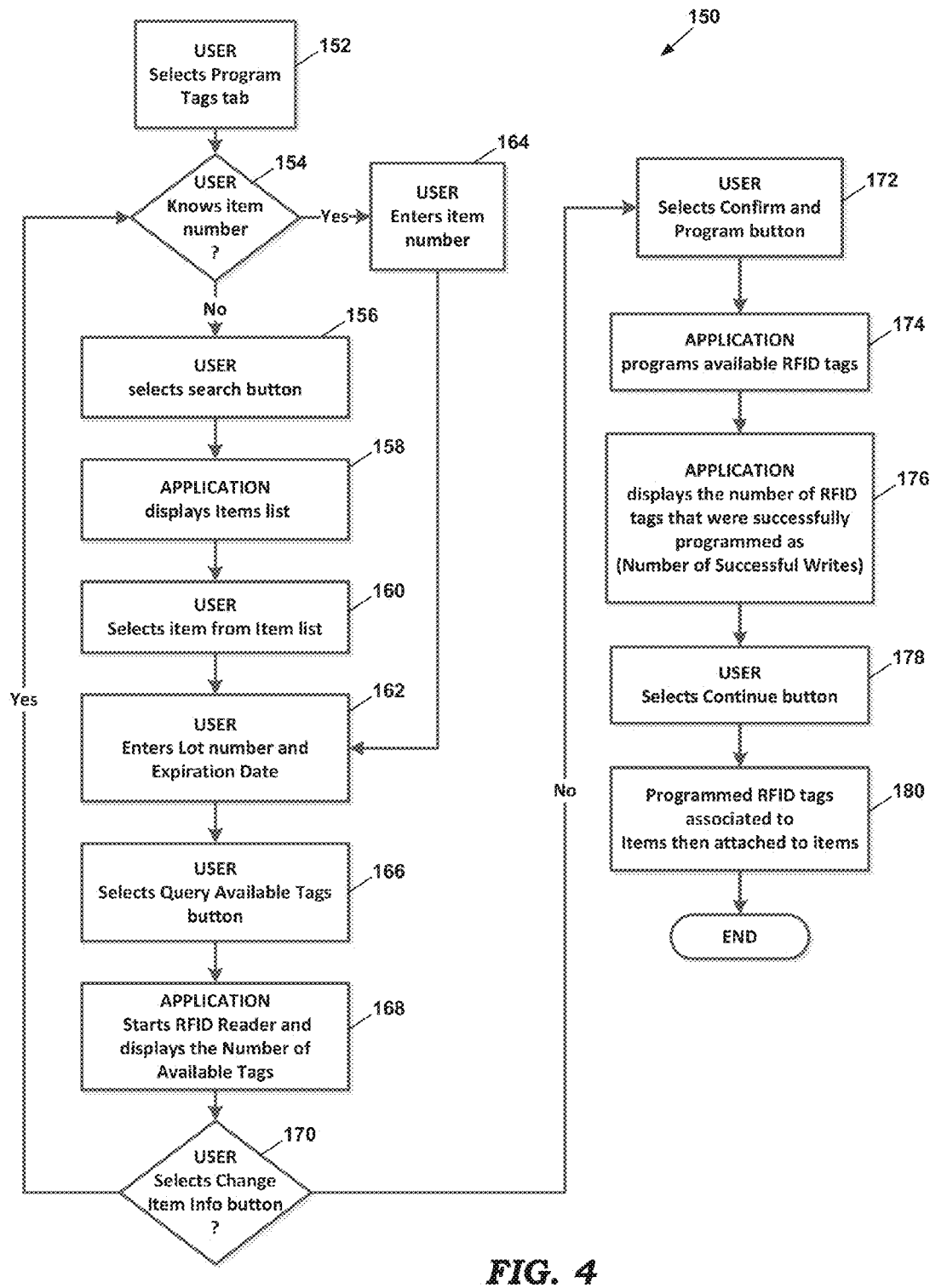
FIG. 4 depicts a method for programming RFID tags for use on medical items according to an embodiment of the invention.
Figure 5A:
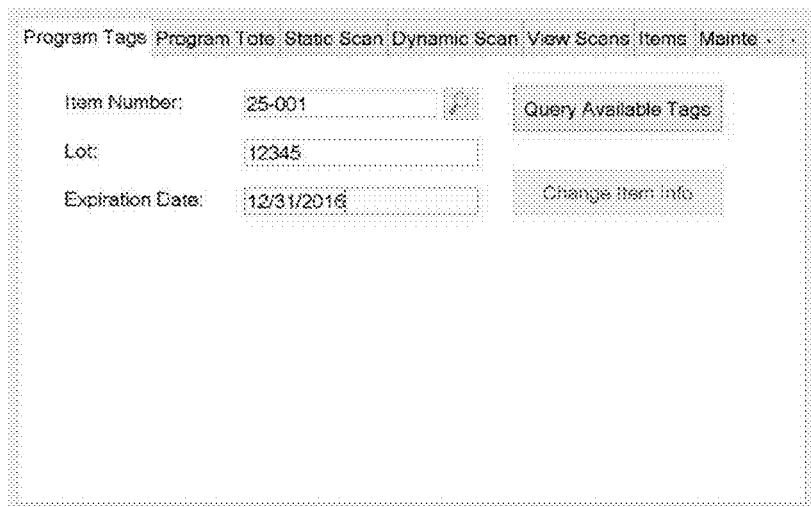
FIGS. 5A-5C depict display screens displayed to a user of the system while performing the method depicted in FIG. 4 according to an embodiment of the invention.
Figure 5B:
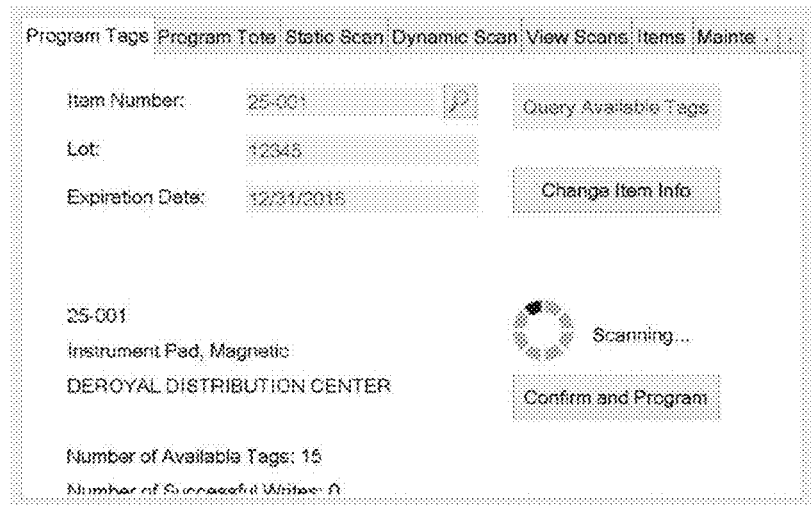
Figure 5C:
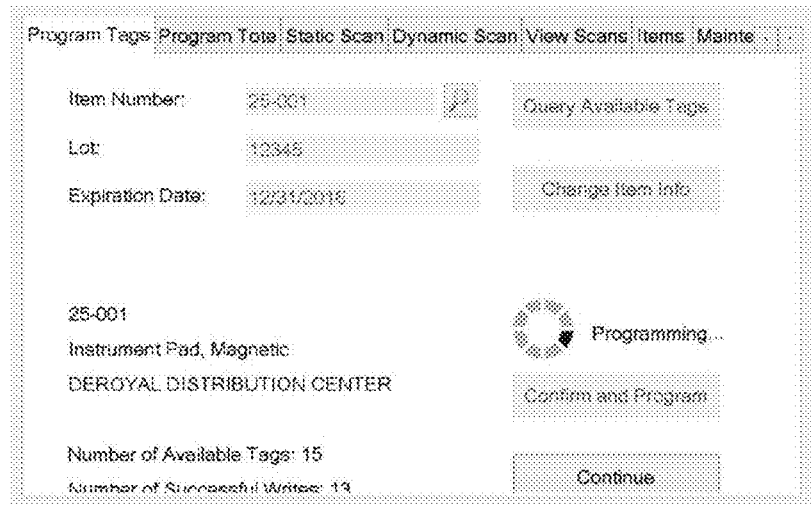

FIG. 4 depicts an embodiment of a method 150 for programming RFID tags for medical items. While running the medical item inventory application, the user selects the "Program Tags" tab on the example display screen depicted in FIG. 5A (step 152). If the user does not know the item number of the medical item for which a tag is to be programmed (step 154), the user may select the "Search" button (step 156). This causes the application to display an items list (step 158) from which the user selects the item (step 160). The user then enters the lot number and expiration date (step 162) and selects the "Query Available Tags" button (step 166). This activates the RFID reader/writer to detect and display a number of tags that are available for programming (step 168). In the example of FIG. 5B, the RFID reader/writer detected fifteen tags available for programming. Before programming the tags with item information, the user has an opportunity to edit the item information (step 170). If the item information is complete and accurate, the user selects the "Confirm and Program" button (step 172). This causes the RFID reader/writer to program the available RFID tags with the item information (step 174). The number of tags that are successfully programmed are indicated as "Number of Successful Writes" as shown in FIG. 5C (step 176). The user then selects the "Continue" button (step 178), which causes the application to associate the newly programmed tags with the item number in the database 52 (step 180).

Figure 6:
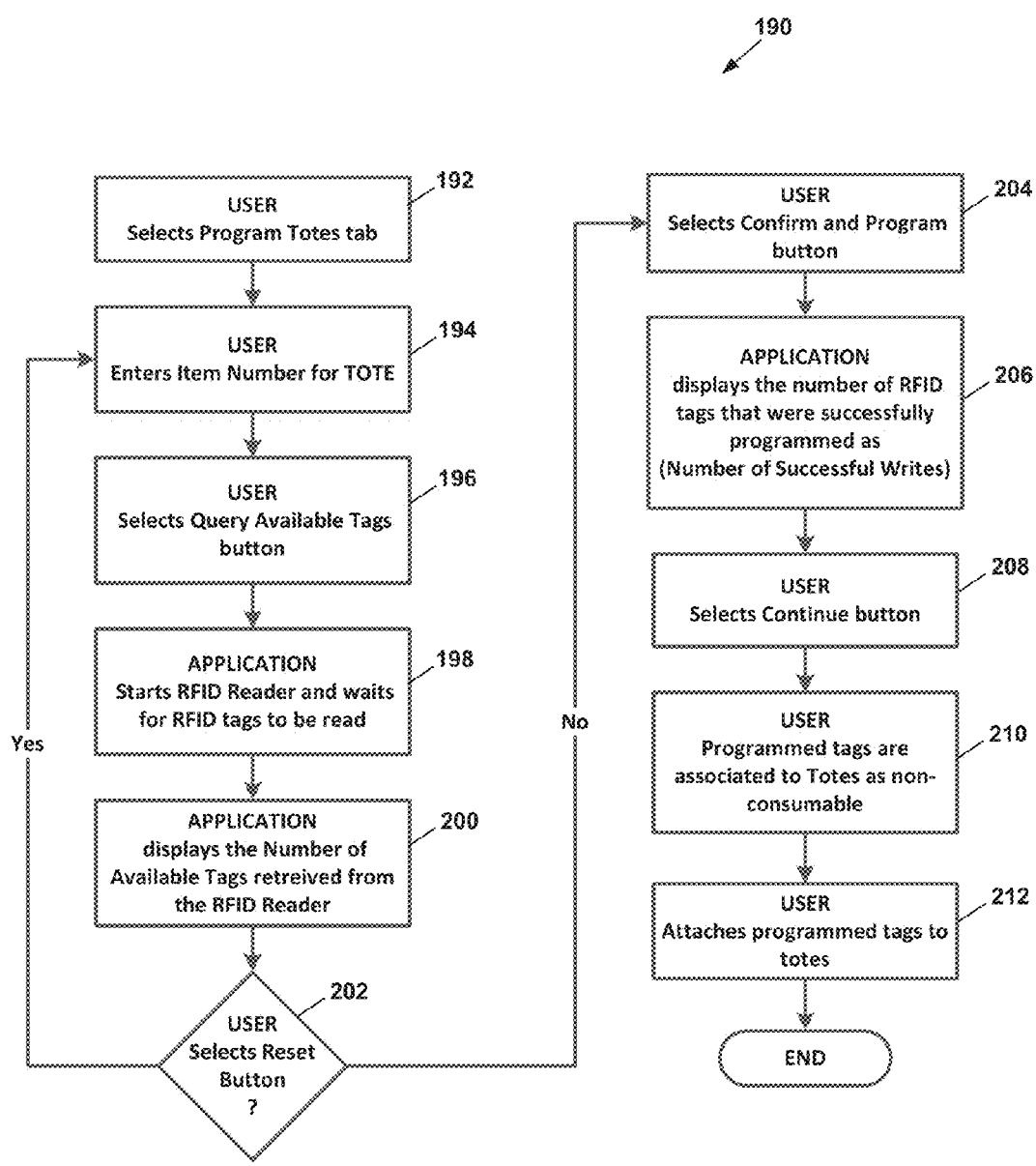
FIG. 6 depicts a method for programming RFID tags for use on storage bins used for carrying medical items according to an embodiment of the invention.
Figure 7A:
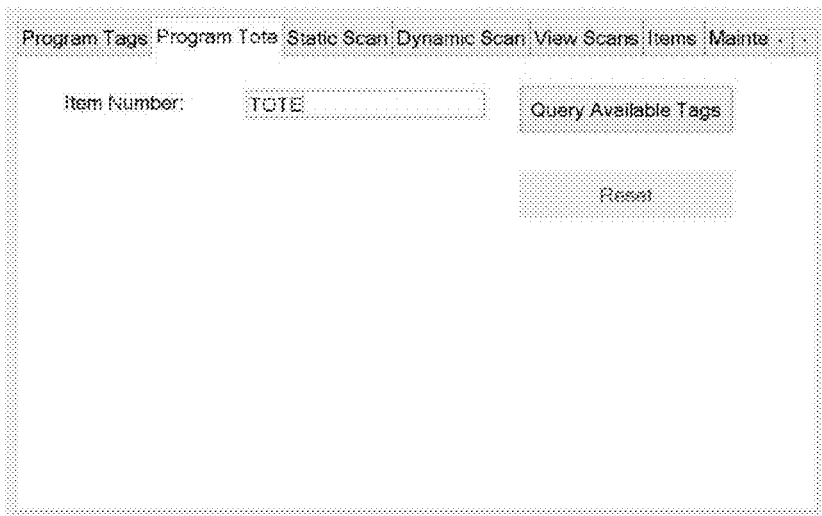
FIGS. 7A-7C depict display screens displayed to a user of the system while performing the method depicted in FIG. 6 according to an embodiment of the invention.
Figure 7B:
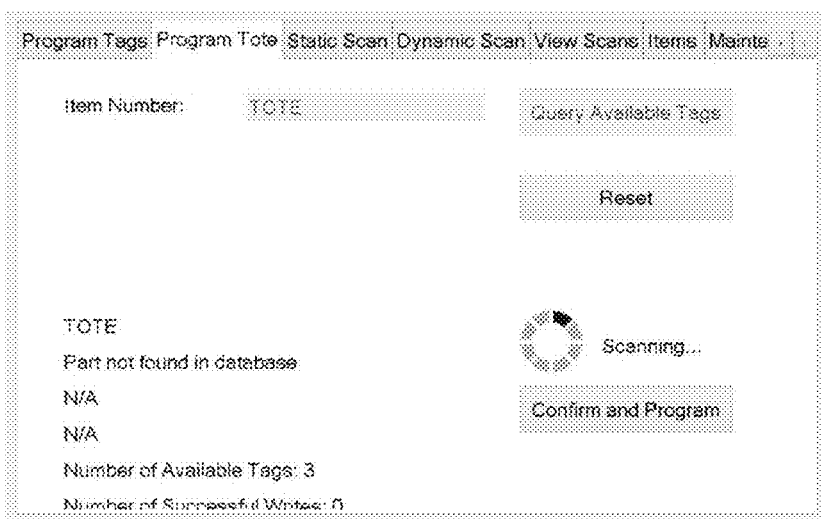
Figure 7C:
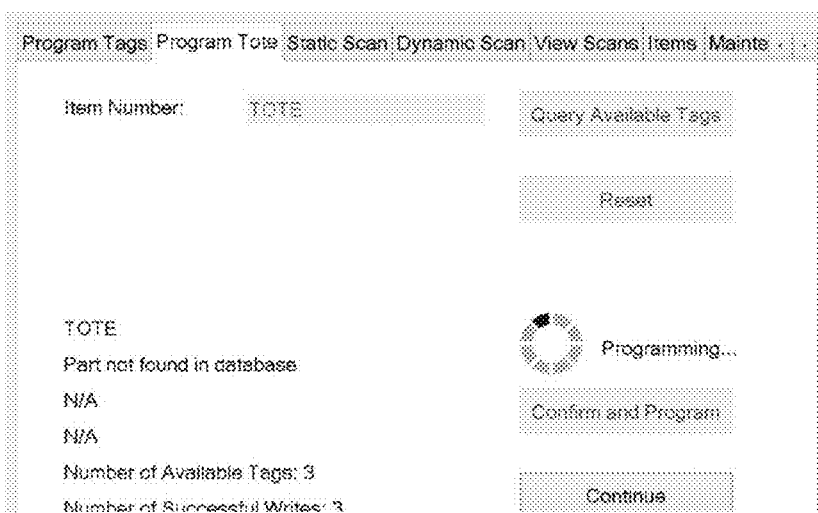

FIG. 6 depicts an embodiment of a method 190 for programming RFID tags for bins or totes, such as the waste bin 18 or the storage bin 34. While running the medical item inventory application, the user selects the "Program Totes" tab on the example display screen depicted in FIG. 6A (step 192). The user then enters the item number for the tote (step 194) and selects the "Query Available Tags" button (step 196). This activates the RFID reader/writer to detect the number of tags that are available for programming (step 198) and display the available number on the display device (step 200). In the example of FIG. 7B, the RFID reader/ writer detected three tags available for programming. If the user wishes to proceed with the programming process, the user selects the "Confirm and Program" button (step 204). This causes the RFID reader/writer to program the available RFID tags with the tote information (step 206). The number of tags that are successfully programmed are indicated as "Number of Successful Writes" as shown in FIG. 7C (step 176). The user then selects the "Continue" button (step 208), which causes the application to associate the newly programmed tags with non-consumable totes in the database 52 (step 210). The programmed tags are then attached to the totes (step 212).

Figure 8:
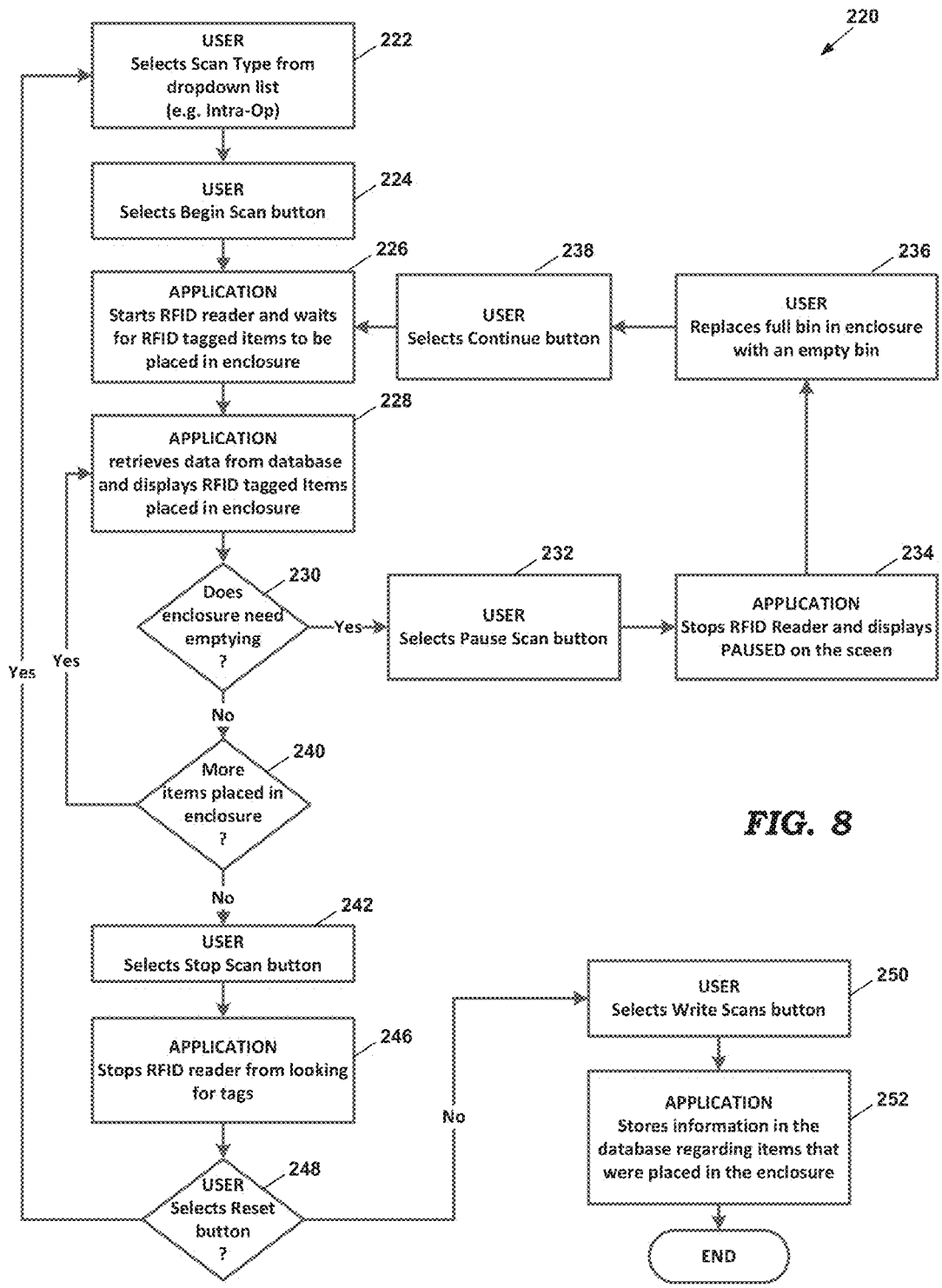
FIG. 8 depicts a method for reading RFID tags on medical items placed in the shielded enclosure according to an embodiment of the invention.
Figure 9A:
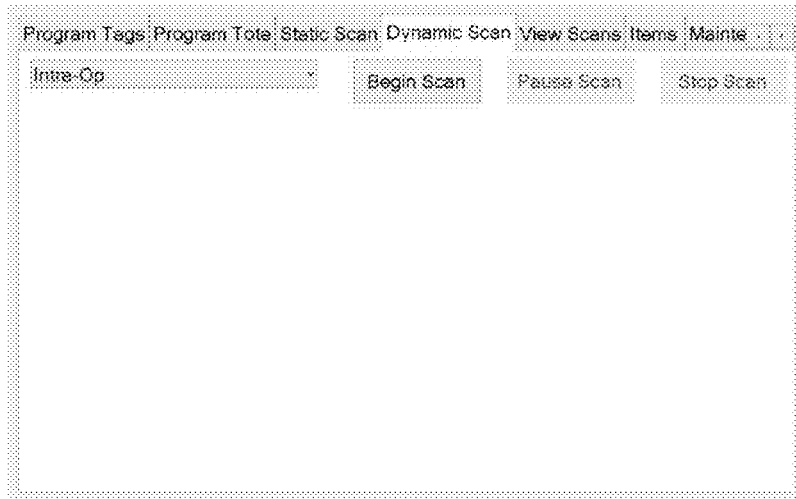
FIGS. 9A-9C depict display screens displayed to a user of the system while performing the method depicted in FIG. 8 according to an embodiment of the invention.
Figure 9B:
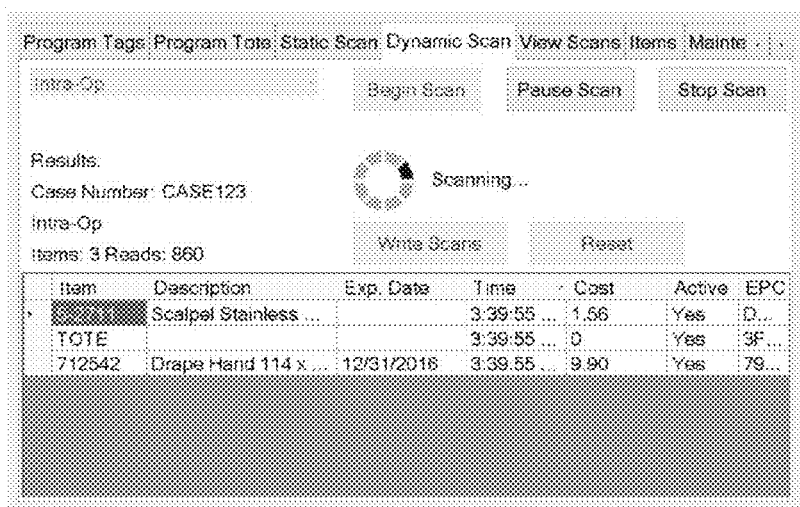
Figure 9C:
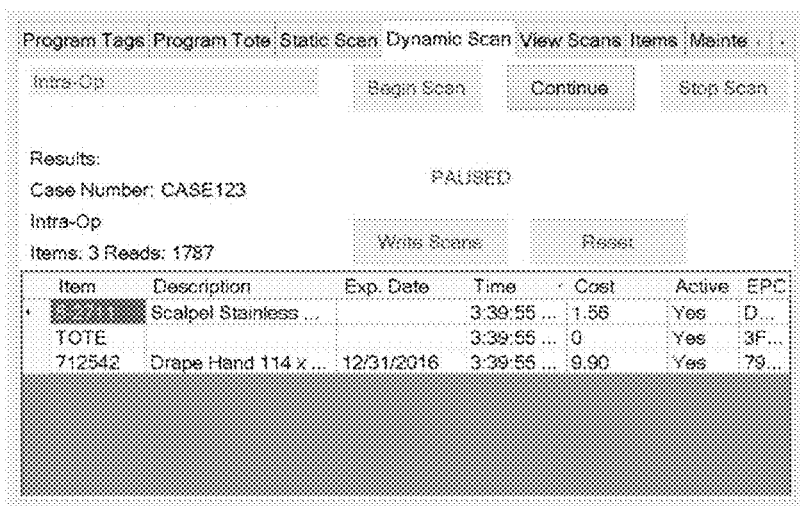

FIG. 8 depicts an embodiment of a method 220 for reading RFID tags on items dropped into the shielded enclosure 12. While running the medical item inventory application, the user selects the "Dynamic Scan" tab on the example display screen depicted in FIG. 9A and selects the scan type, such as "Intra-Op" from the dropdown list (step 222). When the user selects the "Begin Scan" button (step 224), the RFID tag reader 28 is activated and begins reading the tags of any items or item wrappers dropped into the enclosure 12 (step 226). As shown in FIG. 9B, information regarding all tagged items detected by the RFID tag reader is displayed on the display device (step 228). In this example, three tagged items or item wrappers were detected: (1) item 5-2711 Scalpel Stainless . . . , (2) item TOTE, and (3) item 712542 Drape Hand 114 x . . . . If at some point during the medical procedure the waste bin within the enclosure needs to be emptied, the user selects the "Pause Scan" button in FIG. 9B (step 232), which causes the application to stop the RFID tag reader and display "Paused" on the screen as shown in FIG. 9C (step 234). After the full bin has been replaced with an empty bin in the enclosure (step 236), the user selects the "Continue" button (step 238), which causes the RFID tag reader 28 to resume reading the tags of any additional items or item wrappers dropped into the enclosure 12 (step 226). When the medical procedure is complete and no more wrappers are to be dropped into the enclosure 12 (step 240), the user selects the "Stop Scan" button (step 242), which causes the RFID tag reader 28 to cease detecting RFID tags in the enclosure (step 246). The user then selects the "Write Scans" button (step 250) at which point the application stores in the database 52 all the item information regarding items or item wrappers that were placed into the enclosure during the medical procedure (step 252).

Figure 10:
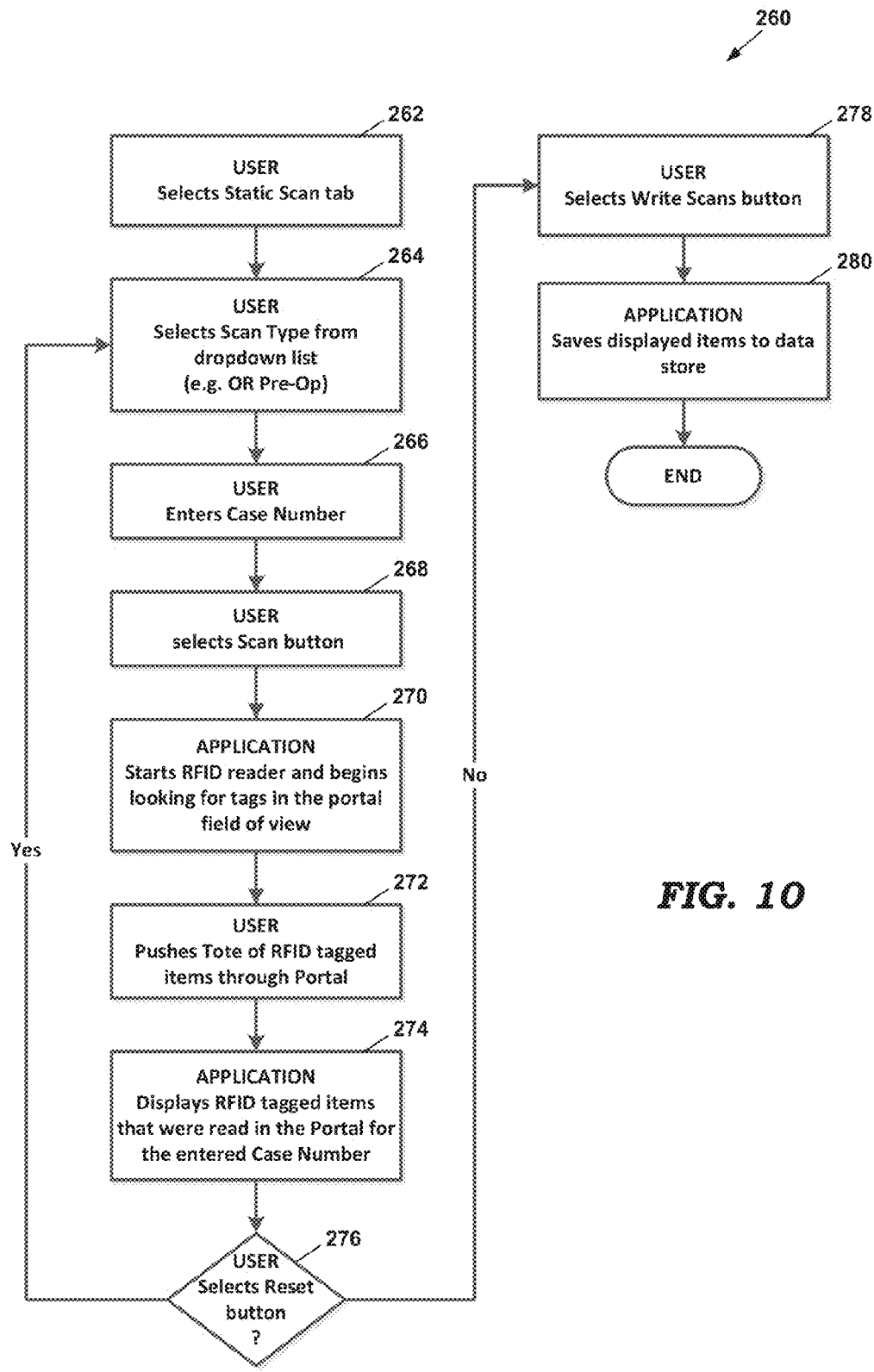
FIG. 10 depicts a method for reading RFID tags on medical items passed through a portal according to an embodiment of the invention.
Figure 11A:
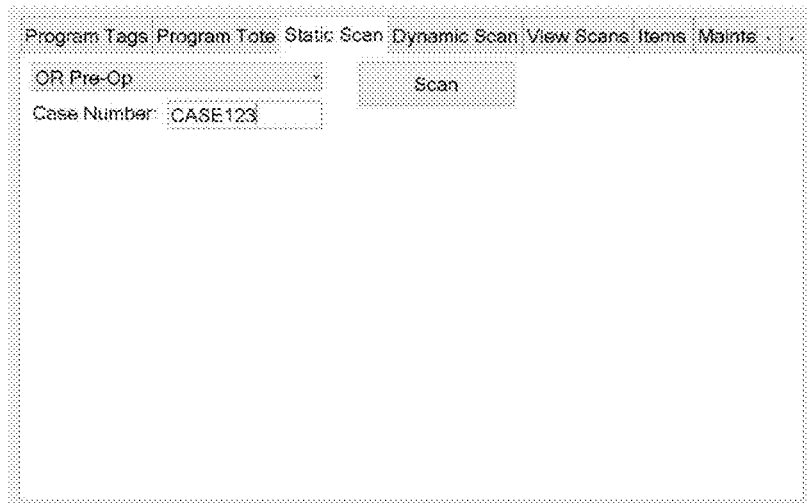
FIGS. 11A-11B depict display screens displayed to a user of the system while performing the method depicted in FIG. 10 according to an embodiment of the invention.
Figure 11B:
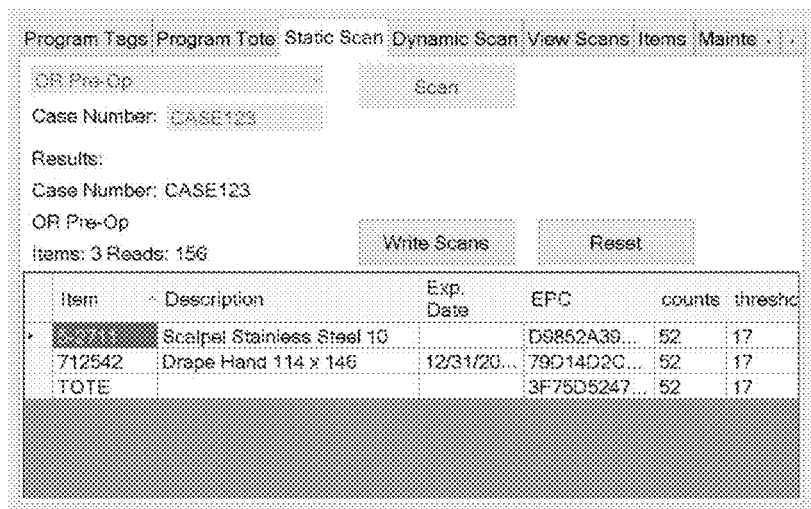

FIG. 10 depicts an embodiment of a method 260 for reading RFID tags on items passed through the portal 48. While running the medical item inventory application, the user selects the "Static Scan" tab (step 262) on the example display screen depicted in FIG. 11A and selects the scan type, such as "OR Pre-Op" from the dropdown list (step 264). The user then enters the case number for the medical procedure (step 266) and selects the "Scan" button (step 268). The application then activates the RFID tag reader 28, which begins reading the tags of any items or item wrappers within the field of view the antennas in the portal opening 49 (step 270). When the user pushes a tote containing RFID-tagged items through the portal opening 49 (step 272), the RFID tag reader 46 reads the tags of the items in the tote and the application displays a list of the items on the display device as shown in FIG. 11B (step 274). The user then selects the "Write Scans" button (step 278) at which point the application stores in the database 52 all the item information regarding items that were passed through the portal (step 280).

Figure 12:
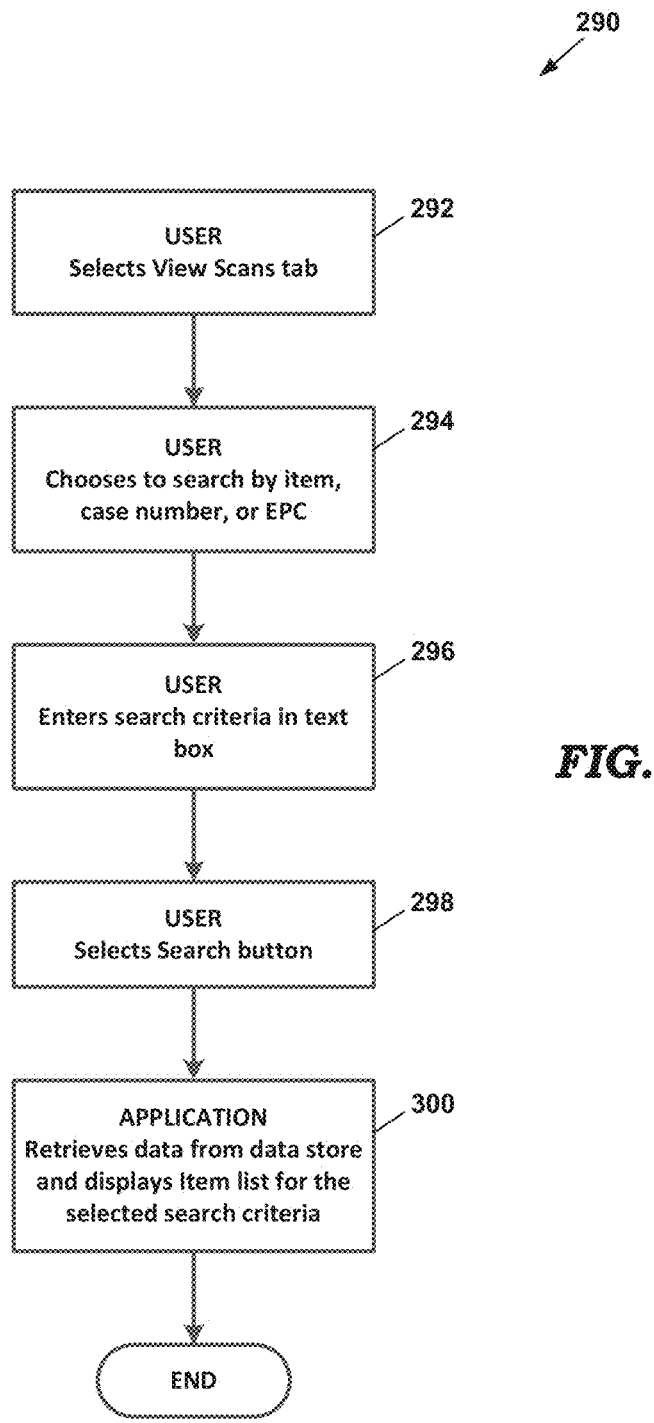
FIG. 12 depicts a method for searching for medical items having RFID tags that have been scanned into the system according to an embodiment of the invention.
Figures 15, 16, 17:
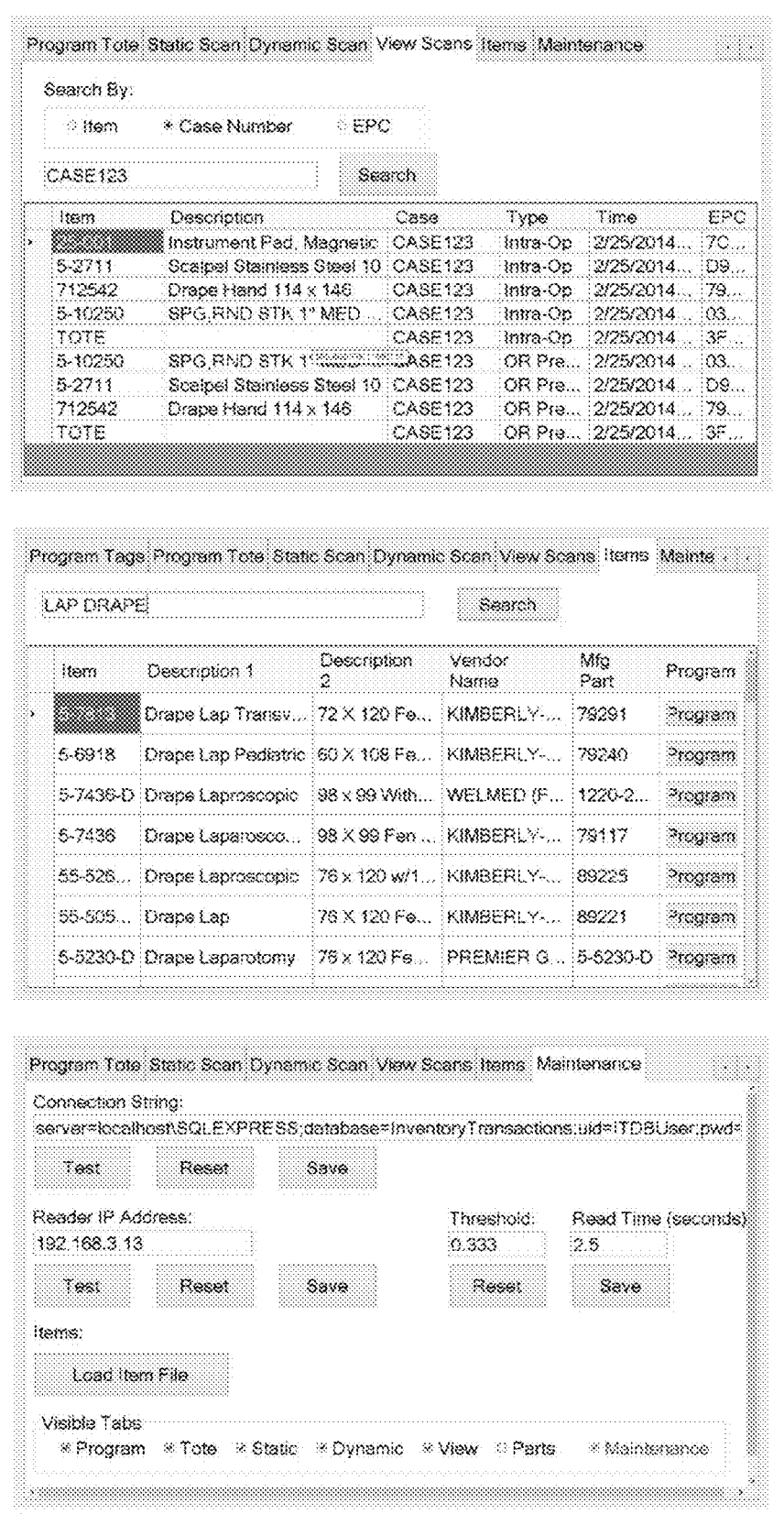

FIG. 12 depicts an embodiment of a method 290 for viewing listings of items whose RFID tags have been read and entered into the database 52. While running the medical item inventory application, the user selects the "View Scans" tab (step 292) on the example display screen as depicted in FIG. 15 and chooses to search by item, by case number or by Electronic Product Code (EPC) (step 294). As will be appreciated by one skilled in the art, the EPC is a unique number that identifies a specific item in the supply chain. When the user enters the search criteria (such as CASE123) in the text box (step 296) and selects the "Search" button (step 298), the application retrieves item information from the database 52 regarding all items scanned in association with CASE123 and displays a list of the item information on the display device as shown in FIG. 15 (step 300).

Figure 13:
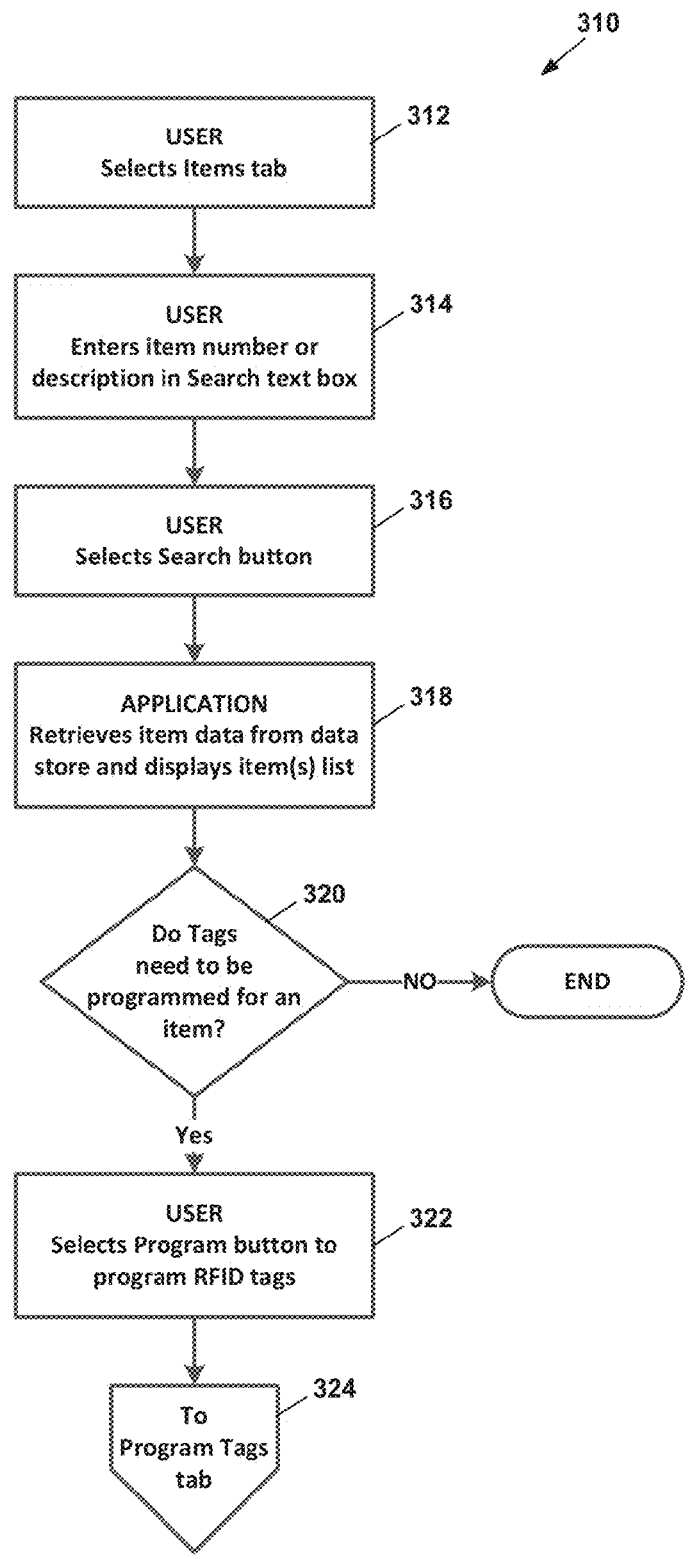
FIG. 13 depicts a method for searching for medical items and retrieving item data according to an embodiment of the invention.

FIG. 13 depicts an embodiment of a method 310 for viewing listings of items having information stored the database 52. While running the medical item inventory application, the user selects the "Items" tab (step 312) on the example display screen as depicted in FIG. 16 and enters an item number or item keywords in the search text box (step 314). When the user selects the "Search" button (step 316), the application retrieves item information regarding all items in the database 52 and displays a list of the item information on the display device as shown in FIG. 16 (step 318). If the list indicates that RFID tags have not yet been programmed for an item (step 320), the user may select the "Program" button (step 322) which will cause the application to display the "Program Tags" tab (step 324).

Figure 14:
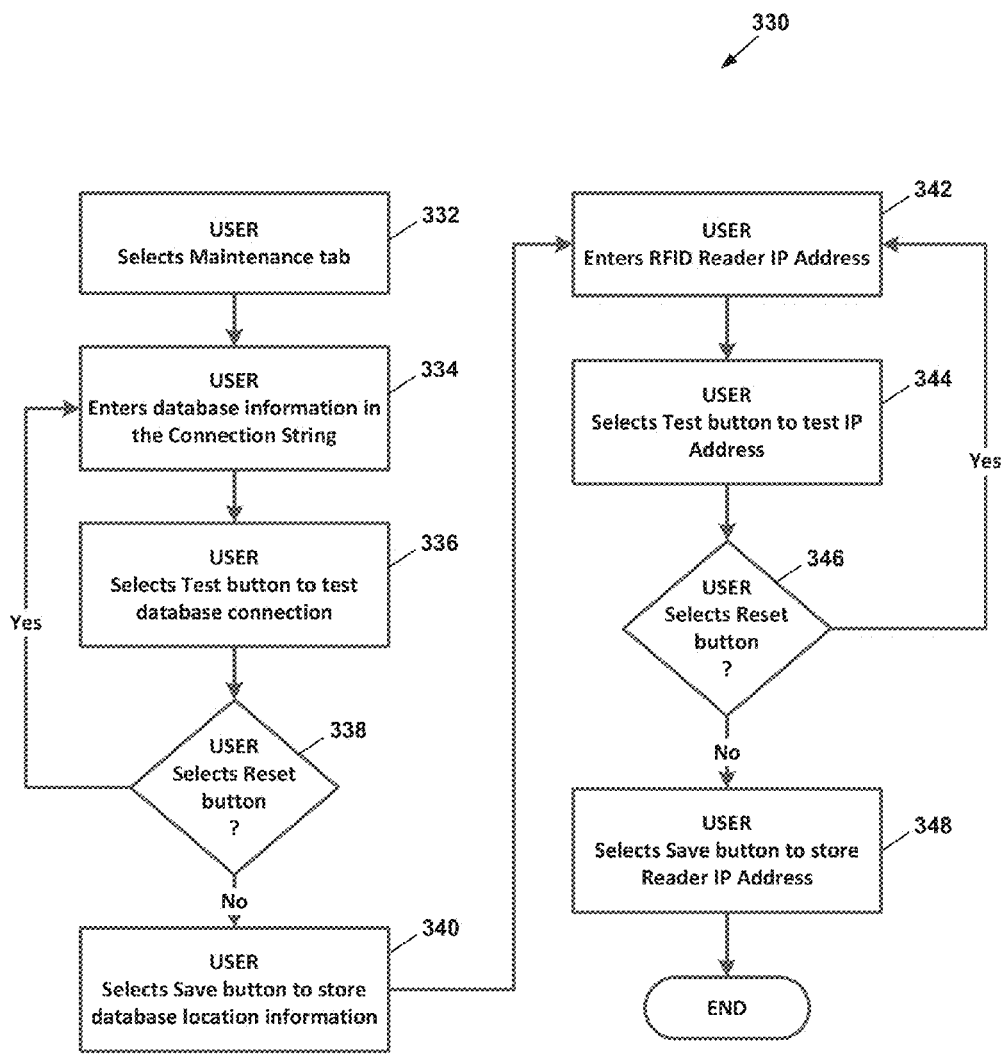
FIG. 14 depicts a method for system maintenance according to an embodiment of the invention.

FIG. 14 depicts an embodiment of a method 330 for performing maintenance tasks related to the database 52 and the LAN 42. While running the medical item inventory application, the user selects the "Maintenance" tab (step 332) on the example display screen as depicted in FIG. 17 and enters the network address of the database 52 (step 334). The user may then select the "Test" button to test the connection to the database 52 (step 336). If the test indicates a successful connection, the user may select the "Save" button to store the database address information (step 340). The "Maintenance" tab also allows the user to test the network connection to the RFID tag reader(s) by entering the IP address in the address box (step 342) and selecting the "Test" button (step 344). If the test indicates a successful connection, the user may select the "Save" button to store the IP address information (step 348).

Figure 19:
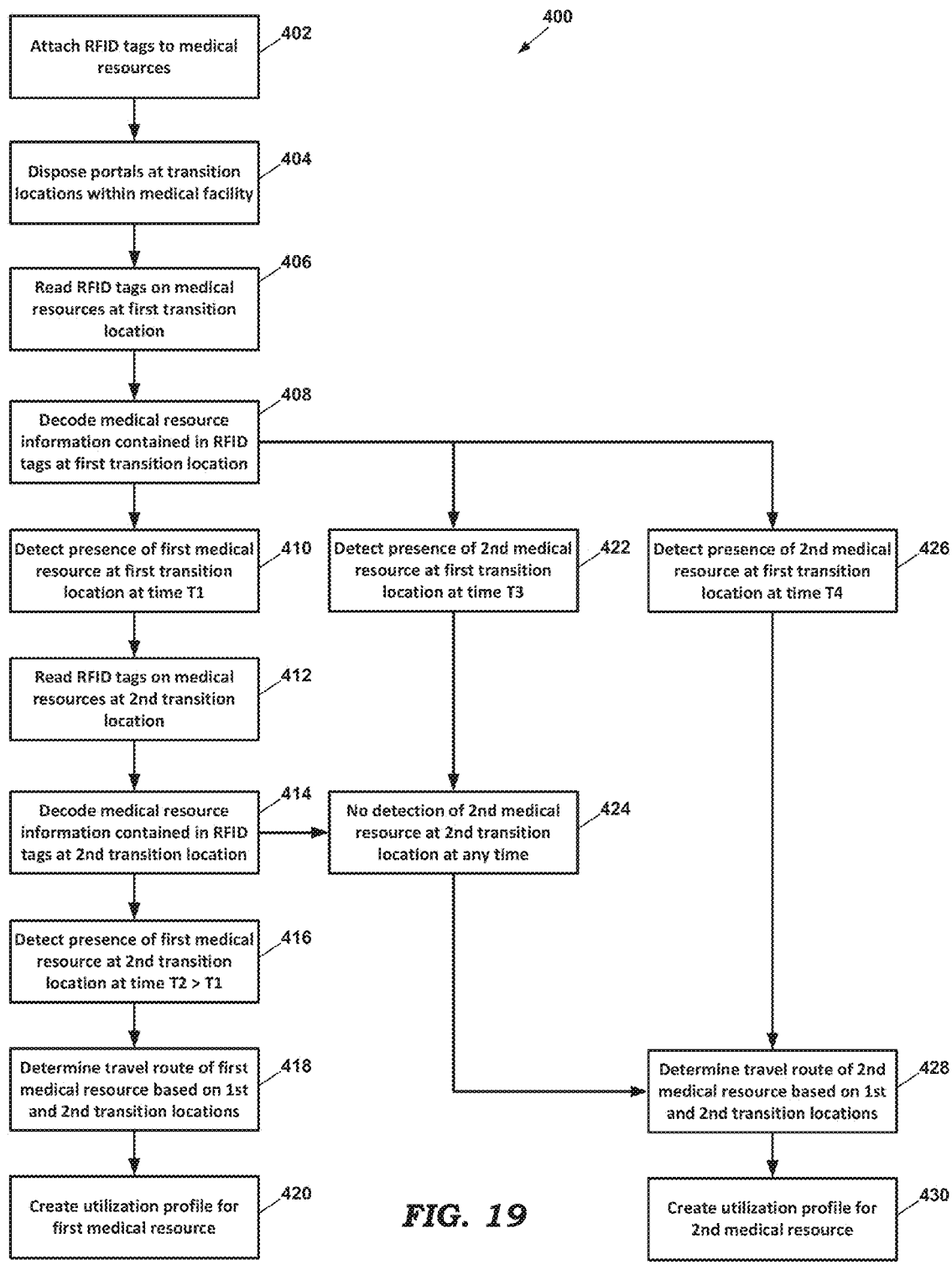
FIGS. 19 and 20 depict processes for sensing and recording utilization of medical resources in the performance of a medical procedure in a medical facility according to embodiments of the invention.

Various embodiments described herein provide systems for sensing RFID tags attached to various medical resources at various transition locations throughout a medical facility, for tracking routes of movement of the medical resources based on the sensing of the RFID tags, for detecting relationships between medical resources based on sensing their RFID tags at the same transition locations during overlapping time periods, for analyzing utilization of the medical resources, and for developing utilization profiles. For example, FIG. 19 depicts an embodiment of a process 400 for analyzing the utilization of two different medical resources based on sensing (or not sensing) their RFID tags at two different transition locations within a medical facility. The process 400 involves attaching RFID tags to medical resources (step 402), disposing RFID-sensing portals at various transition locations within the medical facility (step 404), reading medical resource information from the RFID tags using the portals (step 406 and 412), and decoding the medical resource information to identify the medical resources (step 408 and 414) and determine various characteristics of the resources as described in more detail below.

For example, with continued reference to FIG. 19, a first medical resource is detected at a first transition location at a time T1 (step 410) and at a second transition location at a time T2 (step 416). Based on these detections, the system determines that the first medical resource traveled from the first transition location to the second transition location between times T1 and T2 (step 418). Based on this route of travel and the times of detection, the system creates a utilization profile for the first medical resource (step 420).

A second medical resource is detected at the first transition location at a time T3 (step 422), which may be less than, greater than, or equal to time T1. The second medical resource is again detected at the first transition location at a time T4 (step 426), which is occurs after time T3 (T4>T3). There is no detection of the second medical resource at the second transition location between times T3 and T4 (step 424). Based on these detections, the system determines that the second medical resource traveled from the first transition location back to the first transition location between times T3 and T4, and did not travel to the second transition location (step 428). Based on this route of travel and the times of detection, the system creates a utilization profile for the second medical resource (step 430).

In the example of FIG. 19, the first transition location may be an entrance/exit door of a medical procedure room PR1 within a medical facility, the second transition location may be a waste container WC1 within the medical procedure room PR1, the first medical resource may be a first medical item that was picked to be used during a medical procedure MP1 in the procedure room PR1, and the second medical resource may be a second medical item that was picked to be used during the same medical procedure MP1 in the procedure room PR1. Based on the detections described above, the system determines that the first medical item entered the medical procedure room PR1 (first transition location) at time T1, and it or its wrapper was deposited in the waste container WC1 (second transition location) at time T2. Based on this route of travel, the system creates a utilization profile indicating that the first medical item was used or consumed during the medical procedure MP1. Also based on the detections described above, the system determines that the second medical item entered the medical procedure room PR1 (first transition location) at time T3, exited the medical procedure room PR1 (first transition location) at time T4, and was not deposited in the waste container WC1 (second transition location). Based on this route of travel, the system creates a utilization profile indicating that the second medical item was brought into the medical procedure room PR1, but was not used during the medical procedure MP1.

Figure 20:
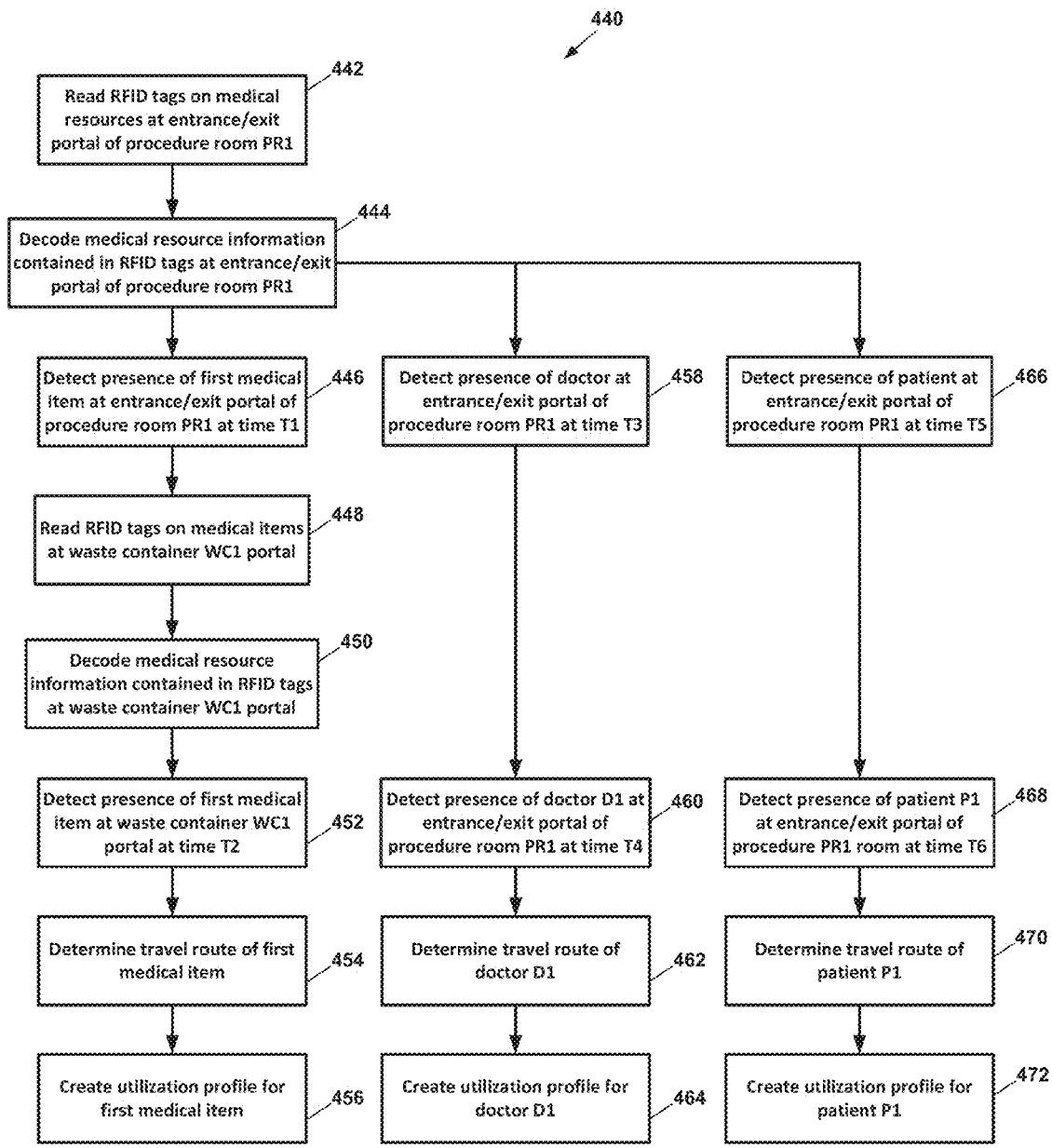

FIG. 20 depicts an embodiment of a process 440 for analyzing the utilization of three different medical resources based on their RFID tags being sensed (or not sensed) at two different transition locations within a medical facility. The process 440 involves reading medical resource information from RFID tags attached to three medical resources—a first medical item, a doctor, and a patient—using portals at the entrance/exit of a procedure room PR1 and on a waste container WC1 (step 442 and 448), and decoding the medical resource information to identify the medical resources (step 444 and 450) and determine various characteristics of the resources. As in the previous example, the system determines that the first medical item entered the medical procedure room PR1 at time T1, and it or its wrapper was deposited in the waste container WC1 at time T2 (step 454). Based on this route of travel, the system creates a utilization profile indicating that the first medical item was used during the medical procedure MP1 (step 456).

With continued reference to FIG. 20, the system detects the doctor D1 entering the medical procedure room PR1 at time T3 which may be less than, greater than, or equal to time T1 (step 458). The doctor D1 is detected leaving the medical procedure room PR1 at time T4 which is greater than T1 and T3 (step 460). Based on this route of travel, the system creates a utilization profile indicating that the doctor D1 was involved in a medical procedure MP1 in the procedure room PR1 between times T3 and T4 (step 464). In preferred embodiments, the utilization profile for the doctor D1 indicates that the first medical item was consumed or used during a medical procedure MP1 performed by the doctor D1. In some embodiments, the utilization profile for the first medical item also indicates that the first medical item was consumed or used during a medical procedure MP1 performed by the particular doctor D1.

With continued reference to FIG. 20, the system detects the patient P1 entering the medical procedure room PR1 at time T5 which may be less than, greater than, or equal to time T1 (step 466). The patient P1 is detected leaving the medical procedure room PR1 at time T6 that is greater than T1 and T5 (step 468). Based on this route of travel, the system creates a utilization profile indicating that the patient P1 was involved in a medical procedure MP1 in the procedure room PR1 between times T5 and T6 (step 470). In preferred embodiments, the utilization profile for the patient P1 also indicates that the first medical item was consumed or used during the medical procedure MP1 performed on the patient P1 by the particular doctor D1. In some embodiments, the utilization profile for the first medical item also indicates that the first medical item was consumed or used during the medical procedure MP1 performed on the particular patient P1. In some embodiments, the utilization profile for the doctor D1 also indicates that the first medical item was consumed or used during the medical procedure MP1 performed on the particular patient P1.

Figure 21:
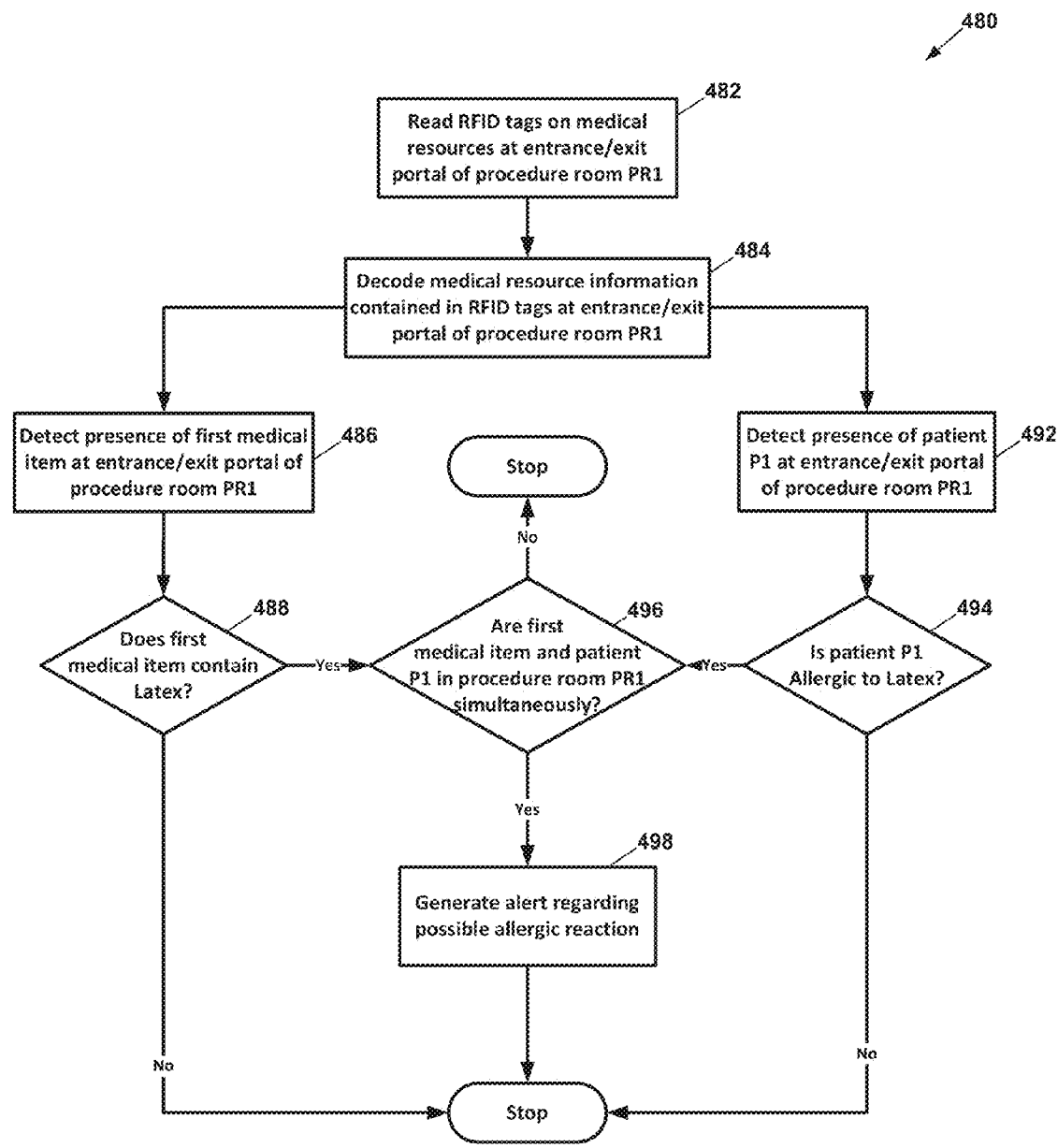
FIGS. 21 and 22 depict processes for generating alerts based on utilization of medical resources in the performance of a medical procedure in a medical facility according to embodiments of the invention.

FIG. 21 depicts a preferred embodiment of a process 480 for generating an alert based on utilization of medical resources in the performance of a medical procedure in a medical facility. This process 480 analyzes the utilization of two different medical resources based on sensing their RFID tags at the same transition location within the medical facility. The process 480 involves reading medical resource information from RFID tags attached to the two medical resources—a first medical item and a patient P1—using portals at the entrance/exit of a procedure room PR1 (step 482), and decoding the medical resource information to identify the medical resources (step 484) and to determine various characteristics of the resources. For example, the medical resource information decoded at step 484 may indicate whether the first medical item contains a potential allergenic, such as Latex, and whether the patient P1 is allergic to any drugs or substances, such as Latex. Using the decoded information, the system detects that the first medical item entered the medical procedure room PR1 (step 486) at a certain time and that the patient P1 entered the medical procedure room PR1 at a certain time (step 492). If the first medical item contains a substance to which the patient P1 is allergic, and the first medical item and the patient P1 are in the procedure room PR1 simultaneously (steps 488, 494 and 496), the system generates an alert informing personnel in the procedure room PR1 of the potential for a harmful allergic reaction (step 498). This alert may be audible (siren) and visible (strobe lights) in the procedure room, and it may be sent via electronic messaging to other personnel within the medical facility to give notice of the situation. In preferred embodiments, the occurrence of such an event is also reflected in the utilization profile of the patient P1.

In some embodiments, the system generates a potential allergic reaction alert if an RFID reader portal at the doorway of a supply room detects a medical item leaving the supply room that was picked for use during a medical procedure involving a patient that is allergic to a substance in the medical item. This detection could also be made by any RFID reader portal at any transition location between the supply room and the medical procedure MOM.

Figure 22:
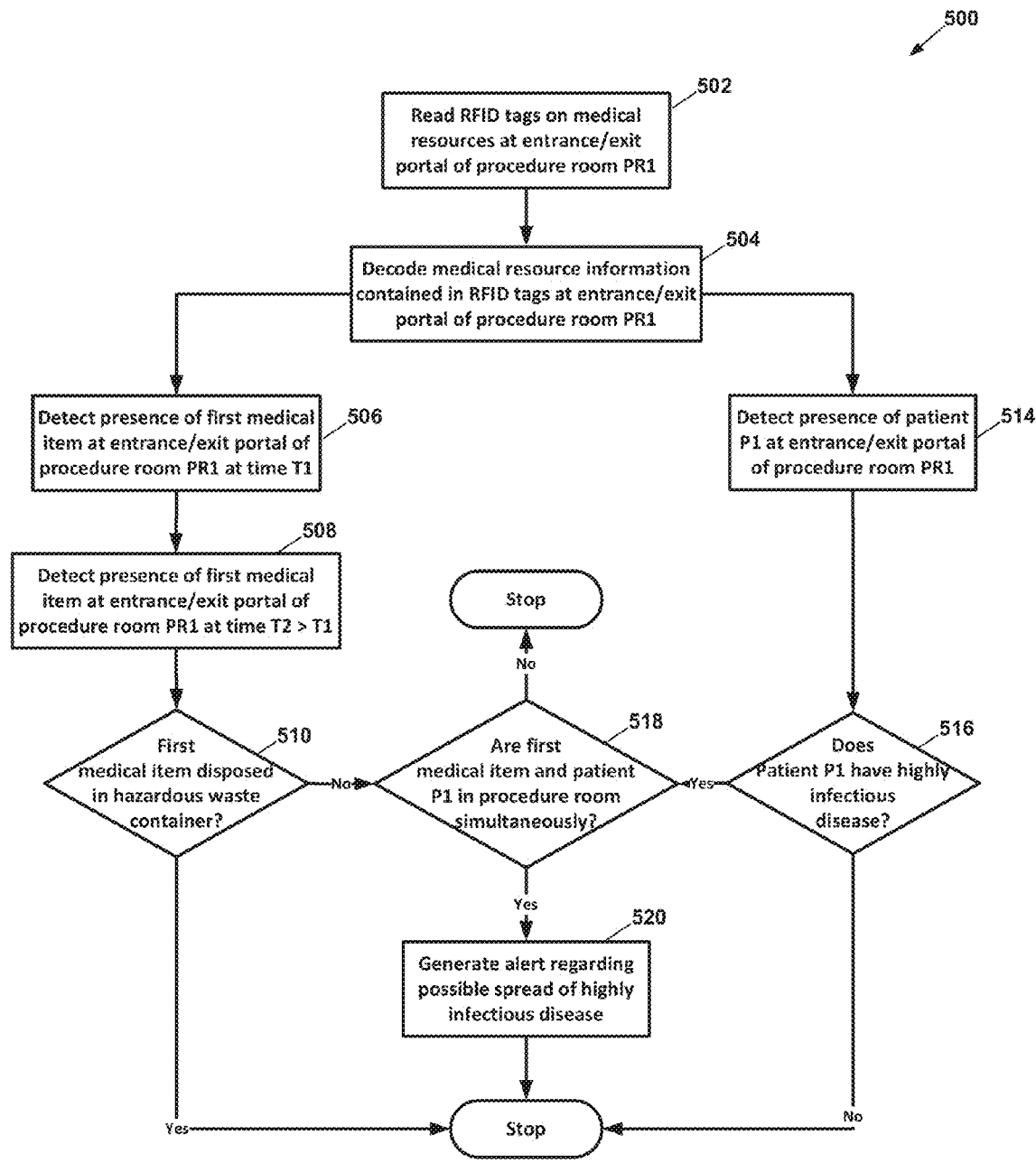

FIG. 22 depicts a preferred embodiment of another process 500 for generating an alert based on utilization of medical resources in the performance of a medical procedure in a medical facility. This process 500 analyzes the utilization of two different medical resources based on sensing their RFID tags at the same transition location within the medical facility. The process 500 involves reading medical resource information from RFID tags attached to the two medical resources—a first medical item and a patient P1—using portals at the entrance/exit of a procedure room PR1 (step 502), and decoding the medical resource information to identify the medical resources (step 504) and to determine various characteristics of the resources. For example, the medical resource information decoded at step 504 may indicate that the patient P1 is infected with a highly infectious contagion, such as Methicillin-resistant *Staphylococcus aureus* (MRSA). Using the decoded information, the system detects that the first medical item entered the medical procedure room PR1 (step 506) at time T1 and that the patient P1 entered the medical procedure room PR1 at a certain time (step 514). The system later detects that the first medical item has exited the medical procedure room PR1 (step 508) at time T2. If the first medical item was not deposited in a hazardous waste container prior to leaving the procedure room PR1, and the first medical item and the patient P1 were in the procedure room PR1 simultaneously, and the patient P1 is infected with a contagion such as MRSA (steps 510, 516, 518), the system generates an alert informing personnel in the procedure room PR1 of a potential for spread of a highly infectious contagion due to possible contact with the first medical item (step 520). This alert may be audible (siren) and visible (strobe lights) in the procedure room, and it may be sent via electronic messaging to other personnel within the medical facility to give notice of the situation. In preferred embodiments, the occurrence of such an event is also reflected in the utilization profile of the first medical item. In some situations, the determination that the patient is infected (step 516) may be made after the procedure is complete and the patient has left the procedure room. In such situations, the system will generate the alert (step 520) after information indicating the patient's infection is entered into the patient's record (the medical resource information for the patient.)

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An apparatus for sensing and recording consumption of medical items during performance of a medical procedure, wherein the medical items are at least initially enclosed in wrappers having RFID tags disposed in or on the wrappers, wherein medical item information regarding the medical items is encoded in the RFID tags, the apparatus comprising:
   a shielded enclosure having an internal space for receiving the wrappers of the medical items, the shielded enclosure configured to attenuate radio frequency signals emanated from RFID tags disposed outside the shielded enclosure to levels that are substantially undetectable within the internal space;
   one or more first RFID antennas for receiving radio frequency signals emanated from RFID tags attached to the wrappers disposed within the internal space, wherein the radio frequency signals contain the medical item information encoded in the RFID tags;
   at least one first RFID reader electrically connected to the one or more first RFID antennas, the at least one first RFID reader for decoding the medical item information contained in the radio frequency signals emanated from the RFID tags;
   a portal having:
      a portal opening through which unused wrappers pass, the unused wrappers enclosing medical items that are available for use; and
      one or more second RFID antennas for receiving radio frequency signals emanated from RFID tags attached to the unused wrappers that pass through the portal; and
   at least one second RFID reader electrically connected to the one or more second RFID antennas of the portal, the at least one second RFID reader for decoding the medical item information contained in the radio frequency signals emanated from the RFID tags that pass through the portal; and
   a computer in electrical communication with the at least one first RFID reader and the at least one second RFID reader, the computer having a processor for executing a medical item inventory module comprising:
      instructions for receiving the medical item information decoded by the at least one first RFID reader and generating a post-op used-item list of medical items consumed during the medical procedure based on the medical item information encoded in the RFID tags attached to used wrappers disposed in the internal space of the shielded enclosure;
      instructions for receiving the medical item information decoded by the at least one second RFID reader and generating a post-op unused-item list of medical items that were not consumed during the medical procedure based on medical item information encoded in RFID tags attached to the unused set of wrappers that pass through the portal; and
      instructions for analyzing the post-op unused-item list of medical items that were not consumed during the medical procedure and post-op unused-item lists generated during multiple other medical procedures of the same type performed by the same doctor to determine trends in the lack of usage of certain medical items listed on Bills of Materials or Doctor Preference Cards.

2. The apparatus of claim 1 further comprising a waste bin that is disposable within the internal space of the shielded enclosure, the waste bin having an open top for receiving the used wrappers that are dropped into the waste bin during performance of the medical procedure.

3. The apparatus of claim 2 wherein the shielded enclosure includes a door in a sidewall of the shielded enclosure, the door covering an opening that is large enough to accommodate the waste bin.

4. The apparatus of claim 3 wherein:
   the shielded enclosure includes a switch disposed adjacent the door, such that opening or closing the door engages the switch to cause a change in state of the switch; and
   the at least one first RFID reader is electrically connected to the switch, wherein a change in state of the switch triggers the at least one first RFID reader to start or stop decoding information encoded in the radio frequency signals emanated from the RFID tags.

5. The apparatus of claim 1 wherein the shielded enclosure includes an aperture through which the used wrappers may be deposited into the internal space as medical items are consumed during performance of the medical procedure, the aperture including means for attenuating radio frequency signals emanated from RFID tags disposed outside the shielded enclosure to levels that are substantially undetectable within the internal space.

6. The apparatus of claim 5 wherein the means for attenuating radio frequency signals emanated from RFID tags disposed outside the shielded enclosure comprise one or more covers disposed over the aperture.

7. The apparatus of claim 1 wherein the medical item inventory module further comprises instructions for recording time information in the post-op used-item list, the time information indicating a time at which each wrapper of the used set of wrappers was deposited into the internal space of the shielded enclosure.

8. The apparatus of claim 1 wherein the medical item inventory module further comprises instructions for generating billing information based on the post-op used-item list of medical items consumed during the medical procedure.

9. The apparatus of claim 1 wherein the medical item inventory module further comprises:
   instructions for comparing the post-op used-item list and the post-op unused-item list to a pre-op list of medical items that were picked from inventory to be consumed during the medical procedure;
   instructions for generating a first alert message if any item in the pre-op list does not appear in at least one of the post-op used-item list and post-op unused-item list; and
   instructions for generating a second alert message if any item in the post-op used-item list or the post-op unused-item list does not appear in the pre-op list.

10. The apparatus of claim 1 wherein the wrappers comprise a pre-op set of wrappers enclosing medical items that were picked from inventory to be consumed during the medical procedure, and wherein:
the portal opening allows passage of the pre-op set of wrappers through the portal prior to beginning the medical procedure; and
the medical item inventory module further comprises instructions for receiving the medical item information decoded by the at least one second RFID reader and generating a pre-op list of medical items that were picked from inventory to be consumed during the medical procedure, the instructions generating the pre-op list based on medical item information encoded in RFID tags attached to the pre-op set of wrappers.

11. The apparatus of claim 1 wherein the portal opening comprises a passageway, an aperture, a window, a doorway, a gateway, a hallway, a pathway, an aisle, or a handheld scanning device.

12. An apparatus for sensing and recording consumption of medical items during performance of a medical procedure, wherein the medical items are at least initially enclosed in wrappers having RFID tags disposed in or on the wrappers, wherein medical item information regarding the medical items is encoded in the RFID tags, the apparatus comprising:
a waste bin having an open top for receiving a first set of wrappers dropped into the waste bin during performance of the medical procedure;
a shielded enclosure configured to attenuate radio frequency signals emanated from RFID tags disposed outside the shielded enclosure to levels that are substantially undetectable within the shielded enclosure, the shielded enclosure having a door covering an opening large enough to accommodate placement of the waste bin into and removal of the waste bin from within the shielded enclosure;
one or more first RFID antennas for receiving radio frequency signals emanated from RFID tags attached to the wrappers disposed in the waste bin, wherein the radio frequency signals contain the medical item information encoded in the RFID tags;
a portal having:
a portal opening; and
one or more second RFID antennas for receiving radio frequency signals emanated from RFID tags attached to wrappers that are passed through the portal; and
at least one RFID reader electrically connected to the first and second RFID antennas, the at least one RFID reader for decoding the medical item information contained in the radio frequency signals emanated from the RFID tags; and
a computer in electrical communication with the at least one RFID reader, the computer having a processor for executing a medical item inventory module comprising:
instructions for receiving the medical item information decoded by the at least one RFID reader;
instructions for generating a post-op used-item list of medical items consumed during the medical procedure based on the medical item information encoded in the RFID tags attached to a used set of wrappers disposed in the waste bin;
instructions for generating a post-op unused-item list of medical items that were not consumed during the medical procedure based on medical item information encoded in RFID tags attached to an unused set of wrappers enclosing medical items that were not consumed during the medical procedure, wherein the unused set of wrappers are passed through the portal opening after completion of the medical procedure;
instructions for comparing the post-op used-item list and the post-op unused-item list to a pre-op list of medical items that were picked from inventory to be consumed during the medical procedure;
instructions for generating a first alert message if any item in the pre-op list does not appear in at least one of the post-op used-item list and post-op unused-item list; and
instructions for generating a second alert message if any item in the post-op used-item list or the post-op unused-item list does not appear in the pre-op list.

13. The apparatus of claim 12 wherein the medical item inventory module further comprises instructions for generating the pre-op list of medical items based on medical item information encoded in RFID tags attached to a pre-op set of wrappers enclosing medical items that were picked from inventory to be consumed during the medical procedure, wherein the pre-op set of wrappers passes through the portal opening prior to beginning the medical procedure.

14. The apparatus of claim 12 wherein the portal opening comprises a passageway, an aperture, a window, a doorway, a gateway, a hallway, a pathway, or an aisle.

15. A method for sensing and recording consumption of medical items during performance of a medical procedure, the method comprising:
(a) picking medical items from inventory that are enclosed in wrappers including RFID tags, wherein medical item information regarding the medical items is encoded in the RFID tags;
(b) passing the medical items picked in step (a) through an opening in a portal;
(c) using one or more RFID antennas disposed in the opening of the portal, receiving radio frequency signals emanated from RFID tags attached to the wrappers of the medical items passed through the opening of the portal;
(d) using an RFID reader electrically connected to the one or more RFID antennas disposed in the opening of the portal, decoding the medical item information contained in the radio frequency signals emanated from the RFID tags;
(e) during performance of the medical procedure, consuming at least some of the medical items picked in step (a);
(f) placing the wrappers of the medical items consumed during performance of the medical procedure into a shielded enclosure;
(g) using one or more RFID antennas disposed in or on the shielded enclosure, receiving radio frequency signals emanated from RFID tags attached to the wrappers disposed in the shielded enclosure, wherein the radio frequency signals contain the medical item information encoded in the RFID tags;
(h) using an RFID reader electrically connected to the one or more RFID antennas disposed in or on the shielded enclosure, decoding the medical item information contained in the radio frequency signals emanated from the RFID tags;
(i) using a computer processor, generating a post-op used-item list of medical items consumed during the medical procedure based on the medical item information encoded in the RFID tags attached to the wrappers disposed in the shielded enclosure;

(j) using a computer processor, generating a pre-op list of medical items picked from inventory to be used during the medical procedure, the pre-op list generated based on the medical item information encoded in the RFID tags attached to the wrappers of the medical items passed through the opening of the portal in step (b);

(k) using a computer processor, generating billing information based on the post-op used-item list of medical items consumed during the medical procedure;

(l) after step (e), passing medical items picked in step (a) that were not consumed during performance of the medical procedure through the opening of the portal;

(m) using the one or more RFID antennas disposed in the opening of the portal, receiving radio frequency signals emanated from RFID tags attached to the wrappers of the medical items passed through the opening of the portal;

(n) using the RFID reader electrically connected to the one or more RFID antennas disposed in the opening of the portal, decoding the medical item information contained in the radio frequency signals emanated from the RFID tags; and (o) using a computer processor, generating a post-op unused-item list of medical items picked from inventory but not used during the medical procedure, the post-op unused-item list generated based on the medical item information encoded in the RFID tags attached to the wrappers of the medical items passed through the opening of the portal in step (l).

16. The method of claim 15 further comprising:

(l) comparing the post-op used-item list and the post-op unused-item list to the pre-op list of medical items that were picked from inventory to be consumed during the medical procedure;

(q) generating a first alert message if any item in the pre-op list does not appear in at least one of the post-op used-item list and post-op unused-item list; and (r) generating a second alert message if any item in the post-op used-item list or the post-op unused-item list does not appear in the pre-op list.

17. The method of claim 15 wherein step (i) further comprises generating the post-op used-item list including time information indicating a time at which each wrapper was deposited into the shielded enclosure.

18. The method of claim 15 wherein step (f) comprises depositing the wrappers of the medical items consumed during performance of the medical procedure into a waste bin and then placing the waste bin containing the wrappers into the shielded enclosure.

19. A method for sensing and recording consumption of medical items during performance of a medical procedure on a patient, the method comprising:

(a) sensing that a medical item having an RFID tag has entered a medical procedure room using at least one first RFID sensor at a portal associated with the room;

(b) sensing that an RFID tag attached to the patient has entered the medical procedure room using the at least one first RFID sensor at the portal, wherein the RFID tag attached to the patient encodes a patient identification number;

(c) storing in a database one or more of a lot identification number and a unique device identification (UDI) number associated with the medical item having the RFID tag, wherein the lot identification number identifies a manufacturer's lot number for the medical item;

(d) storing in the database the patient identification number associated with the patient;

(e) sensing that the medical item having the RFID tag has been consumed during the medical procedure using at least one second RFID sensor associated with a waste container located in the room; and (f) based on sensing that the medical item has been consumed during performance of the medical procedure and sensing that the RFID tag attached to the patient has entered the medical procedure room, automatically associating in the database the patient identification number with one or more of the lot identification number and the unique device identification (UDI) number.

20. The method of claim 19 further comprising:

(g) storing in the database a doctor identification number associated with a doctor involved with performance of the medical procedure; and (h) associating in the database the item identification number and the doctor identification number based on sensing that the medical item was consumed during performance of the medical procedure.

21. The method of claim 20 wherein step (h) is based at least in part on sensing that an RFID tag attached to the doctor has entered the medical procedure room using the at least one first RFID sensor at the portal, wherein the RFID tag attached to the doctor encodes the doctor identification number.

22. The method of claim 19 further comprising:

(g) determining that the medical item having one or more of the lot identification number and the unique device identification (UDI) number associated in the database with the patient identification number is subject to a manufacturer recall; and (h) based on the determination of step (g), generating an alert directed to the attention of medical personnel, the alert providing notice of the manufacture recall of the medical item.

23. A method for sensing and recording utilization of medical resources in performance of a medical procedure in a medical facility, the method comprising:

(a) attaching an RFID tag to each of a plurality of medical resources, each RFID tag containing medical resource information that uniquely identifies the medical resource to which the RFID tag is attached, the plurality of medical resources including a wrapper of a first medical item and a wrapper of a second medical item;

(b) disposing a first portal to detect RFID tags that enter and exit a medical procedure room within the medical facility, the first portal comprising a first portal opening and one or more first RFID antennas having fields of view directed to the first portal opening;

(c) disposing a second portal to detect only RFID tags that enter a waste container in the medical procedure room, the second portal comprising a second portal opening and one or more second RFID antennas having fields of view directed to the second portal opening;

(d) the one or more first RFID antennas receiving radio frequency signals emanated from the RFID tag attached to the wrapper of the first medical item and the RFID tag attached to the wrapper of the second medical item as the first medical item and the second medical item pass through the first portal opening;

(e) the one or more second RFID antennas receiving radio frequency signals emanated from the RFID tag attached to the wrapper of the first medical item as the wrapper of the first medical item passes through the second portal opening;

(f) decoding first medical resource information contained in the radio frequency signals emanated from the RFID tag attached to the wrapper of the first medical item and decoding second medical resource information contained in the radio frequency signals emanated from the RFID tag attached to the wrapper of the second medical item;

(g) detecting the presence of the first and second medical items within the medical procedure room at a first time, the detecting based on the first and second medical resource information decoded from the radio frequency signals emanated from the RFID tags attached to the wrappers of the first and second medical items passing through the first portal opening, thereby indicating that the first and second medical items have entered the medical procedure room;

(h) detecting the presence of the wrapper of the first medical item within the waste container at a second time that is subsequent to the first time, the detecting based on the first medical resource information decoded from the radio frequency signals emanated from the RFID tag attached to the wrapper of the first medical item passing through the second portal opening, thereby indicating that the first medical item was used or consumed during the medical procedure;

(i) determining a first travel route of the first medical item based at least in part on detection of the first medical item entering the medical procedure room at the first time and detection of the wrapper of the first medical item within the waste container at the second time;

(j) the one or more first RFID antennas receiving radio frequency signals emanated from the RFID tag attached to the wrapper of the second medical item as the second medical item passes through the first portal opening while exiting the medical procedure room at a third time that is subsequent to the first time, thereby indicating that the second medical item exited the medical procedure room at the third time without being used or consumed;

(k) determining a second travel route of the second medical item based at least in part on detection of the second item entering the medical procedure room at the first time and detection of the second medical item exiting the medical procedure room at the third time;

(l) creating a first utilization profile for the first medical item based on the first travel route, the first utilization profile indicating that the first medical item was used or consumed during performance of the medical procedure in the medical procedure room; and (m) creating a second utilization profile for the second medical item based on the second travel route, the second utilization profile indicating that the second medical item entered the medical procedure room but was not used or consumed during performance of the medical procedure, and subsequently exited the medical procedure room.

24. The method of claim 23 further comprising:

(n) disposing a third portal at a doorway to a supply room within the medical facility, the third portal comprising a third portal opening and one or more third RFID antennas having fields of view directed to the third portal opening;

(o) prior to step (d), receiving radio frequency signals emanated from the RFID tag attached to the wrapper of the first medical item as the first medical item exits the supply room;

step (i) comprising determining that the first medical item exited the supply room and subsequently the first medical item entered the medical procedure room; and step (l) comprising creating the first utilization profile further indicating that the first medical item was transferred from the supply room to the medical procedure room to be used during performance of the medical procedure.

25. The method of claim 23 wherein:

step (a) comprises attaching an RFID tag to a patient on which the medical procedure is to be performed;

step (d) comprises the one or more first RFID antennas receiving radio frequency signals emanated from the RFID tag attached to the patient as the patient passes through the first portal opening;

step (f) comprises decoding third medical resource information contained in the radio frequency signals emanated from the RFID tag attached to the patient;

step (g) comprises detecting the presence of the patient within the medical procedure room based on the third medical resource information; and step (l) comprises creating the first utilization profile indicating that the first medical item entered the medical procedure room and was used during performance of the medical procedure on the patient identified by the third medical resource information.

26. The method of claim 23 wherein:

step (a) comprises attaching an RFID tag to a doctor who is to perform the medical procedure;

step (d) comprises the one or more first RFID antennas receiving radio frequency signals emanated from the RFID tag attached to the doctor as the doctor passes through the first portal opening;

step (f) comprises decoding fourth medical resource information contained in the radio frequency signals emanated from the RFID tag attached to the doctor;

step (g) comprises detecting the presence of the doctor within the medical procedure room based on the fourth medical resource information; and step (l) comprises creating the first utilization profile indicating that the first medical item entered the medical procedure room and was used during performance of the medical procedure by the doctor who entered the medical procedure room.

27. A method for sensing and recording utilization of medical resources in performance of a medical procedure in a medical procedure room of a medical facility, the method comprising:

(a) attaching an RFID tag to a medical item, the RFID tag containing medical resource information that uniquely identifies the medical item;

(b) attaching an RFID tag to a patient on which the medical procedure is to be performed;

(c) disposing a portal at an entrance to the medical procedure room to detect RFID tags that enter and exit the medical procedure room, the portal comprising a portal opening and one or more RFID antennas having fields of view directed to the portal opening;

(d) the one or more RFID antennas receiving radio frequency signals emanated from the RFID tag attached to the medical item and the RFID tag attached to the patient as the medical item and the patient pass through the portal opening;

(e) decoding first medical resource information contained in the radio frequency signals emanated from the RFID tag attached to the medical item, wherein the first medical resource information indicates that the medical item contains a first substance;

(f) decoding second medical resource information contained in the radio frequency signals emanated from the RFID tag attached to the patient, wherein the second medical resource information indicates that the patient is allergic to the first substance;

(g) determining that the medical item containing the first substance entered the medical procedure room and the patient who is allergic to the first substance entered the medical procedure room; and (h) upon making the determination of step (g), automatically generating an alert directed to the attention of medical personnel, the alert warning of danger of an allergic reaction due to simultaneous presence of the medical item and the patient in the medical procedure room.

28. A method for sensing and recording utilization of medical resources in performance of a medical procedure in a medical procedure room of a medical facility, the method comprising:

(a) attaching an RFID tag to a medical item, the RFID tag containing medical resource information that uniquely identifies the medical item;

(b) attaching an RFID tag to a patient on which the medical procedure is to be performed;

(c) disposing a portal at an entrance to the medical procedure room to detect RFID tags that enter and exit the medical procedure room, the portal comprising a portal opening and one or more RFID antennas having fields of view directed to the portal opening;

(d) the one or more RFID antennas receiving radio frequency signals emanated from the RFID tag attached to the medical item and the RFID tag attached to the patient as the medical item and the patient pass through the portal opening;

(e) decoding first medical resource information contained in the radio frequency signals emanated from the RFID tag attached to the medical item;

(f) decoding second medical resource information contained in the radio frequency signals emanated from the RFID tag attached to the patient, wherein the second medical resource information indicates that the patient carries a highly infectious contagion;

(g) based on the first and second medical resource information, determining that the medical item and the patient were simultaneously present in the medical procedure room;

(h) receiving radio frequency signals emanated from the RFID tag attached to the medical item as the medical item exits the procedure room; and (i) generating an alert directed to the attention of medical personnel, the alert warning of danger of possible spread of the highly infectious contagion due to simultaneous presence of the medical item and the patient in the medical procedure room without proper disposal of the medical item in a waste container.

* * * * *